(12) United States Patent
Muller et al.

(10) Patent No.: US 11,607,197 B2
(45) Date of Patent: Mar. 21, 2023

(54) INTER-ELEMENT MATRIX IN ULTRASOUND CONTRAST AGENTS POPULATIONS TO MEASURE TRANSPORT PARAMETERS

(71) Applicants: NORTH CAROLINA STATE UNIVERSITY, Raleigh, NC (US); THE UNIVERSITY OF NORTH CAROLINA AT CHAPEL HILL, Chapel Hill, NC (US)

(72) Inventors: Marie Muller, Raleigh, NC (US); Paul Dayton, Raleigh, NC (US); Aditya Joshi, Raleigh, NC (US)

(73) Assignees: THE UNIVERSITY OF NORTH CAROLINA AT CHAPEL HILL, Chapel Hill, NC (US); NORTH CAROLINA STATE UNIVERSITY, Raleigh, NC (US)

(*) Notice: Subject to any disclaimer, the term of this patent is extended or adjusted under 35 U.S.C. 154(b) by 0 days.

(21) Appl. No.: 16/767,188

(22) PCT Filed: Nov. 27, 2018

(86) PCT No.: PCT/US2018/062654
§ 371 (c)(1),
(2) Date: May 27, 2020

(87) PCT Pub. No.: WO2019/104340
PCT Pub. Date: May 31, 2019

(65) Prior Publication Data
US 2020/0359998 A1   Nov. 19, 2020

Related U.S. Application Data

(60) Provisional application No. 62/591,174, filed on Nov. 27, 2017.

(51) Int. Cl.
*A61B 8/08* (2006.01)
*A61B 5/02* (2006.01)
(Continued)

(52) U.S. Cl.
CPC ........ *A61B 8/5223* (2013.01); *A61B 5/02007* (2013.01); *A61B 5/4839* (2013.01); *A61B 8/481* (2013.01); *G06T 7/0012* (2013.01)

(58) Field of Classification Search
CPC . A61B 8/5223; A61B 5/02007; A61B 5/4839; A61B 8/481; A61B 8/5207;
(Continued)

(56) References Cited

U.S. PATENT DOCUMENTS 5,567,415 A    10/1996  Porter
6,450,961 B1    9/2002  Shiki et al.
(Continued)

OTHER PUBLICATIONS

Recchia et al., Sensitive Detection of Abnormal Aortic Architecture in Marfan Syndrome With High-Frequency Ultrasonic Tissue Characterization, vol. 91, Issue 4, Feb. 15, 1995; pp. 1036-1043.*
(Continued)

*Primary Examiner* — Bo Joseph Peng
(74) *Attorney, Agent, or Firm* — Meunier Carlin & Curfman LLC

(57) ABSTRACT

Systems and methods for measuring micro-architectural properties of vascular networks are described herein. An example method can include injecting an ultrasound contrast agent into a medium, and transmitting a plurality of acoustic pulses into the medium using a ultrasound transducer array. Each respective acoustic pulse can be transmitted from one or more elements of the ultrasound transducer array. The method can also include receiving a plurality of backscattered signals with the ultrasound transducer array in response to each respective acoustic pulse, and obtaining a
(Continued)

response matrix including the backscattered signals. The method can further include extracting a coherent or incoherent contribution to the backscattered signals from the response matrix, and quantifying a property of a vascular network based on the coherent or incoherent contribution to the backscattered signals.

20 Claims, 28 Drawing Sheets

(51) Int. Cl.
    *A61B 5/00* (2006.01)
    *G06T 7/00* (2017.01)
(58) Field of Classification Search
    CPC ........... A61B 8/12; A61B 8/08; A61B 8/0891; A61B 8/4472; G06T 7/0012; G06T 2207/10132; G06T 2207/30101; G16H 50/30; A61K 49/223
    See application file for complete search history.

(56) References Cited

U.S. PATENT DOCUMENTS

| | | | |
|---|---|---|---|
| 8,708,909 B2 | 4/2014 | Goertz et al. | |
| 2005/0182324 A1* | 8/2005 | Angelsen | A61B 8/481 600/437 |
| 2008/0281205 A1* | 11/2008 | Naghavi | A61B 8/12 600/458 |
| 2011/0125014 A1* | 5/2011 | Derode | G01S 15/006 600/437 |
| 2016/0262727 A1* | 9/2016 | Dayton | A61K 49/222 |
| 2017/0080255 A1 | 3/2017 | Law et al. | |

OTHER PUBLICATIONS

Derode et al., Ultrasonic imaging of highly scattering media from local measurements of the diffusion constant: Separation of coherent and incoherent intensities, Physical Review E 75, 026602, 2007.*
Lediju et al., Short-lag spatial coherence of backscattered echoes: imaging characteristics, IEEE Trans Ultrason Ferroelectr Freq Control, Jul. 2011;58(7):1377-88.*
Li et al., Visualization of Small-Diameter Vessels by Reduction of Incoherent Reverberation with Coherent Flow Power Doppler, IEEE Trans Ultrason Ferroelectr Freq Control. Nov. 2016; 63(11): 1878-1889.*
Al Murri, A. M., et al. "The relationship between the systemic inflammatory response, tumour proliferative activity, T-lymphocytic and macrophage infiltration, microvessel density and survival in patients with primary operable breast cancer." British journal of cancer 99.7 (2008): 1013-1019.
Appis, Andrew W., Melissa J. Tracy, and Steven B. Feinstein. "Update on the safety and efficacy of commercial ultrasound contrast agents in cardiac applications." Echo research and practice 2.2 (2015): R55-R62.
Aubry, Alexandre, and Arnaud Derode. "Ultrasonic imaging of highly scattering media from local measurements of the diffusion constant: Separation of coherent and incoherent intensities." Physical Review E 75.2 (2007): 026602.
Balleyguier, Corinne, et al. "New potential and applications of contrast-enhanced ultrasound of the breast: Own investigations and review of the literature." European journal of radiology 69.1 (2009): 14-23.
Berg, Wendie A., et al. "Combined screening with ultrasound and mammography vs mammography alone in women at elevated risk of breast cancer." Jama 299.18 (2008): 2151-2163.
Boschi, Federico, et al. "Tumor microvasculature observed using different contrast agents: a comparison between Gd-DTPA-Albumin and B-22956/1 in an experimental model of mammary carcinoma." Magnetic Resonance Materials in Physics, Biology and Medicine 21.3 (2008): 169-176.
Bretagne, Alice, Arnaud Tourin, and Valentin Leroy. "Enhanced and reduced transmission of acoustic waves with bubble meta-screens." Applied Physics Letters 99.22 (2011): 221906.
Busch, K., C. M. Soukoulis, and E. N. Economou. "Transport and scattering mean free paths of classical waves." Physical Review B 50.1 (1994): 93.
Carmeliet, P., "Angiogenesis in life, disease and medicine.," Nature, vol. 438, No. 7070, pp. 932-936, Dec. 2005.
Carmeliet, Peter, and Rakesh K. Jain. "Angiogenesis in cancer and other diseases." nature 407.6801 (2000): 249-257.
Chatterjee, Dhiman, and Kausik Sarkar. "A Newtonian rheological model for the interface of microbubble contrast agents." Ultrasound in medicine & biology 29.12 (2003): 1749-1757.
Church, Charles C. "The effects of an elastic solid surface layer on the radial pulsations of gas bubbles." The Journal of the Acoustical Society of America 97.3 (1995): 1510-1521.
Concato, John, et al. "Molecular markers and mortality in prostate cancer." BJU international 100.6 (2007): 1259-1263.
Crum, L. A., et al. "Acoustic cavitation produced by microsecond pulses of ultrasound: a discussion of some selected results." The Journal of the Acoustical Society of America 91.2 (1992): 1113-1119.
D'Onofrio, Mirko, et al. "Pancreatic multicenter ultrasound study (PAMUS)." European Journal of Radiology 81.4 (2012): 630-638.
De Jong, N., R. Cornet, and C. T. Lancee. "Higher harmonics of vibrating gas-filled microspheres. Part two: Measurements." Ultrasonics 32.6 (1994): 455-459.
De Jong, N., R. Cornet, and CT de Lancée. "Higher harmonics of vibrating gas-filled microspheres. Part one: simulations." Ultrasonics 32.6 (1994): 447-453.
De Jong, Nico, and L. Hoff. "Ultrasound scattering properties of Albunex microspheres." Ultrasonics 31.3 (1993): 175-181.
De Jong, Nico, et al. "Absorption and scatter of encapsulated gas filled microspheres: theoretical considerations and some measurements." Ultrasonics 30.2 (1992): 95-103.
Doinikov, Alexander A., and Paul A. Dayton. "Maxwell rheological model for lipid-shelled ultrasound microbubble contrast agents." The Journal of the Acoustical Society of America 121.6 (2007): 3331-3340.
Du, Hualong, Kaustav Mohanty, and Marie Muller. "Microstructural characterization of trabecular bone using ultrasonic backscattering and diffusion parameters." The Journal of the Acoustical Society of America 141.5 (2017): EL445-EL451.
Eberhard, Anne, et al. "Heterogeneity of angiogenesis and blood vessel maturation in human tumors: implications for antiangiogenic tumor therapies." Cancer research 60.5 (2000): 1388-1393.
Ehling, Josef, et al. "Micro-CT imaging of tumor angiogenesis: quantitative measures describing micromorphology and vascularization." The American journal of pathology 184.2 (2014): 431-441.
Fillon, Mike. "Contrast-enhanced ultrasound may aid prostate cancer detection." (2013): 444-446.
Folkman, Judah, David M. Long Jr, and Frederick F. Becker. "Growth and metastasis of tumor in organ culture." Cancer 16.4 (1963): 453-467.
Fujimoto, James G., et al. "Optical coherence tomography: an emerging technology for biomedical imaging and optical biopsy." Neoplasia 2.1-2 (2000): 9-25.
Gasparini, Giampietro, et al. "Tumor microvessel density, p53 expression, tumor size, and peritumoral lymphatic vessel invasion are relevant prognostic markers in node-negative breast carcinoma." Journal of clinical oncology 12.3 (1994): 454-466.
Gessner, Ryan C., et al. "Acoustic angiography: a new imaging modality for assessing microvasculature architecture." International journal of biomedical imaging 2013 (2013).936593.
Gessner, Ryan, et al. "High-resolution, high-contrast ultrasound imaging using a prototype dual-frequency transducer: in vitro and in vivo studies." IEEE transactions on ultrasonics, ferroelectrics, and frequency control 57.8 (2010): 1772-1781.
Gramiak, Raymond, and Pravin M. Shah. "Echocardiography of the aortic root." Investigative radiology 3.5 (1968): 356-366.

(56) References Cited

OTHER PUBLICATIONS

Guillermo H. Goldsztein "The collapse and rebound of a gas bubble." Studies in Applied Mathematics 112:101-132, 1952.
Hilgenfeldt, Sascha, Detlef Lohse, and Michael Zomack. "Response of bubbles to diagnostic ultrasound: a unifying theoretical approach." The European Physical Journal B—Condensed Matter and Complex Systems 4.2 (1998): 247-255.
Hoff, Lars, Per C. Sontum, and Jens M. Hovem. "Oscillations of polymeric microbubbles: Effect of the encapsulating shell." The Journal of the Acoustical Society of America 107.4 (2000): 2272-2280.
Jain, Rakesh K. "Antiangiogenesis strategies revisited: from starving tumors to alleviating hypoxia." Cancer cell 26.5 (2014): 605-622.
Jain, Rakesh K., John D. Martin, and Triantafyllos Stylianopoulos. "The role of mechanical forces in tumor growth and therapy." Annual review of biomedical engineering 16 (2014): 321-346.
Joshi, Aditya, et al. "An iterative fullwave simulation approach to multiple scattering in media with randomly distributed microbubbles." Physics in Medicine & Biology 62.10 (2017): 4202.
Kedar, Rajendra P., et al. "Microbubble contrast agent for color Doppler US: effect on breast masses. Work in progress." Radiology 198.3 (1996): 679-686.
Keller, Joseph B., and Ignace I. Kolodner. "Damping of underwater explosion bubble oscillations." Journal of applied physics 27.10 (1956): 1152-1161.
Keller, Joseph B., and Michael Miksis. "Bubble oscillations of large amplitude." The Journal of the Acoustical Society of America 68.2 (1980): 628-633.
Klibanov, Alexander L. "Microbubble contrast agents: targeted ultrasound imaging and ultrasound-assisted drug-delivery applications." Investigative radiology 41.3 (2006): 354-362.
Lee, Seunghyung, et al. "Three-dimensional reconstruction of neovasculature in solid tumors and basement membrane matrix using ex vivo X-ray microcomputed tomography." Microcirculation 21.2 (2014): 159-170.
Leroy, Valentin, et al. "Sound velocity and attenuation in bubbly gels measured by transmission experiments." The Journal of the Acoustical Society of America 123.4 (2008): 1931-1940.
Leroy, Valentin, et al. "Transmission of ultrasound through a single layer of bubbles." The European Physical Journal E 29.1 (2009): 123-130.
Li, Chuan-Yuan, et al. "Initial stages of tumor cell-induced angiogenesis: evaluation via skin window chambers in rodent models." Journal of the National Cancer Institute 92.2 (2000): 143-147.
Li, Qian, et al. "Modeling complicated rheological behaviors in encapsulating shells of lipid-coated microbubbles accounting for nonlinear changes of both shell viscosity and elasticity." Physics in Medicine & Biology 58.4 (2013): 985.
Maresca, David, et al. "Imaging microvasculature with contrast-enhanced ultraharmonic ultrasound." Ultrasound in medicine & biology 40.6 (2014): 1318-1328.
Marmottant, Philippe, et al. "A model for large amplitude oscillations of coated bubbles accounting for buckling and rupture." The Journal of the Acoustical Society of America 118.6 (2005): 3499-3505.
Mast, T. Douglas, et al. "Simulation of ultrasonic pulse propagation through the abdominal wall." The Journal of the Acoustical Society of America 102.2 (1997): 1177-1190.
Mast, T. Douglas. "Two-and three-dimensional simulations of ultrasonic propagation through human breast tissue." Acoustics Research Letters Online 3.2 (2002): 53-58.
Mézière, Fabien, et al. "Measurements of ultrasound velocity and attenuation in numerical anisotropic porous media compared to Biot's and multiple scattering models." Ultrasonics 54.5 (2014): 1146-1154.
Morgan, Karen E., et al. "Experimental and theoretical evaluation of microbubble behavior: Effect of transmitted phase and bubble size." IEEE transactions on ultrasonics, ferroelectrics, and frequency control 47.6 (2000): 1494-1509.

Neppiras, E. A., and B. E. Noltingk. "Cavitation produced by ultrasonics: theoretical conditions for the onset of cavitation." Proceedings of the Physical Society. Section B 64.12 (1951): 1032.
Nico, Beatrice, et al. "Evaluation of microvascular density in tumors, pro and contra." Histology and histopathology (2008): 601-607.
Noltingk, B. Eo, and Eo A. Neppiras. "Cavitation produced by ultrasonics." Proceedings of the Physical Society. Section B 63.9 (1950): 674-685.
Page, J. H., et al. "Diffusive transport of acoustic waves in strongly scattering media." Physica B: Condensed Matter 263 (1999): 37-39.
Paul, Shirshendu, et al. "Determination of the interfacial rheological properties of a poly (DL-lactic acid)-encapsulated contrast agent using in vitro attenuation and scattering." Ultrasound in medicine & biology 39.7 (2013): 1277-1291.
Paul, Shirshendu, et al. "Material characterization of the encapsulation of an ultrasound contrast microbubble and its subharmonic response: Strain-softening interfacial elasticity model." The Journal of the Acoustical Society of America 127.6 (2010): 3846-3857.
Pinton, Gianmarco F., et al. "A heterogeneous nonlinear attenuating full-wave model of ultrasound." IEEE transactions on ultrasonics, ferroelectrics, and frequency control 56.3 (2009): 474-488.
Pinton, Gianmarco F., Gregg E. Trahey, and Jeremy J. Dahl. "Sources of image degradation in fundamental and harmonic ultrasound imaging using nonlinear, full-wave simulations." IEEE transactions on ultrasonics, ferroelectrics, and frequency control 58.4 (2011): 754-765.
Plesset, Milton S. "The dynamics of cavitation bubbles." Journal of applied mechanics 16 (1949): 277-282.
Prosperetti, A. (1994). "Bubble dynamics: Some things we did not know 10 years ago," in Bubble Dynamics and Interface Phenomena: Proceedings of an IUTAM Symposium held in Birmingham, U.K., Sep. 1993, pp. 3-16.
Rayleigh, Lord. "VIII. On the pressure developed in a liquid during the collapse of a spherical cavity." The London, Edinburgh, and Dublin Philosophical Magazine and Journal of Science 34.200 (1917): 94-98.
Salem, Imen Ben, et al. "Propagation of ultrasound in aqueous foams: bubble size dependence and resonance effects." Soft Matter 9.4 (2013): 1194-1202.
Setola, S. V., et al. "Contrast-enhanced sonography of the kidney." Abdominal imaging 32.1 (2007): 21-28.
Sever, Ali R., et al. "Preoperative sentinel node identification with ultrasound using microbubbles in patients with breast cancer." American Journal of Roentgenology 196.2 (2011): 251-256.
Shelton, Sarah E., et al. "Molecular acoustic angiography: a new technique for high-resolution superharmonic ultrasound molecular imaging." Ultrasound in medicine & biology 42.3 (2016): 769-781.
Shelton, Sarah E., et al. "Quantification of microvascular tortuosity during tumor evolution using acoustic angiography." Ultrasound in medicine & biology 41.7 (2015): 1896-1904.
Sirsi, Shashank R., et al. "Contrast ultrasound imaging for identification of early responder tumor models to anti-angiogenic therapy." Ultrasound in medicine & biology 38.6 (2012): 1019-1029.
Snoeks, T. J. A., C. W. G. M. Löwik, and E. L. Kaijzel. "'In vivo' optical approaches to angiogenesis imaging." Angiogenesis 13.2 (2010): 135-147.
Streeter, Jason E., et al. "Improving sensitivity in ultrasound molecular imaging by tailoring contrast agent size distribution: in vivo studies." Molecular imaging 9.2 (2010): 87-95.
Stride, Eleanor, and Nader Saffari. "Investigating the significance of multiple scattering in ultrasound contrast agent particle populations." ieee transactions on ultrasonics, ferroelectrics, and frequency control 52.12 (2005): 2332-2345.
Tourin, Arnaud, et al. "Transport parameters for an ultrasonic pulsed wave propagating in a multiple scattering medium." The Journal of the Acoustical Society of America 108.2 (2000): 503-512.
Vakoc, Benjamin J., et al. "Cancer imaging by optical coherence tomography: preclinical progress and clinical potential." Nature Reviews Cancer 12.5 (2012): 363-368.
Van der Bij, S., et al. "Markers for the non-invasive diagnosis of mesothelioma: a systematic review." British journal of cancer 104.8 (2011): 1325-1333.

(56) References Cited

OTHER PUBLICATIONS

Weidner, Noel, et al. "Tumor angiogenesis and metastasis—correlation in invasive breast carcinoma." New England Journal of Medicine 324.1 (1991): 1-8.
Weidner, Noel, et al. "Tumor angiogenesis: a new significant and independent prognostic indicator in early-stage breast carcinoma." JNCI: Journal of the National Cancer Institute 84.24 (1992): 1875-1887.
Yun, Seok-Hyun, et al. "High-speed optical frequency-domain imaging." Optics express 11.22 (2003): 2953-2963.
Zabolotskaya, E. A. "Quasi-plane waves, in the nonlinear acoustics of confined beams." Sov. Phys. Acoust. 15 (1969): 35-40.
International Preliminary Report on Patentability issued for Application No. PCT/US2018/062654, dated Jun. 11, 2020.
International Search Report and Written Opinion issued in corresponding PCT application No. PCT/US2018/062654, dated Jan. 24, 2019, 10 pages.
Joshi et al. In-vivo quantitative analysis of the angiogenic microvasculature in tumor-bearing rats using multiple scattering. Proceedings of Meetings on Acoustics 29, 020003 (2016); doi: 10.1121/2,0000449. [retrieved on May 1, 2019]. Retrieved from the internet. <URL: https://asa.scitation.org/doi/10.1121/1.4970022>.

* cited by examiner

| STAGE | DETAILS | METHOD |
|---|---|---|
| Iteration 0: Primary interactions | Scattering of incident pulse (or incident pulse scattered from one bubble to other) by bubbles | FDTD simulation of propogation |
| Iteration 1: Primary radiation | Acoustic radiation from bubbles in response to primary interactions | Paul-Sarkar model |
| Senondary interactions (Primary radiation as additive source) | Primary interactions + Scattering of primary radiation | FDTD simulation of propogation (with additive sources) |
| Iteration 2: Secondary radiation | Acoustic radiation from bubbles in response to secondary interactions | Paul-Sarkar model |
| Secondary interactions (Primary & secondary radiations as additive sources) | Primary interactions + Scattering of primary radiation + Scattering of primary radiation | FDTD simulation of propogation (with additive sources) |

FIG. 5

FIG. 13A
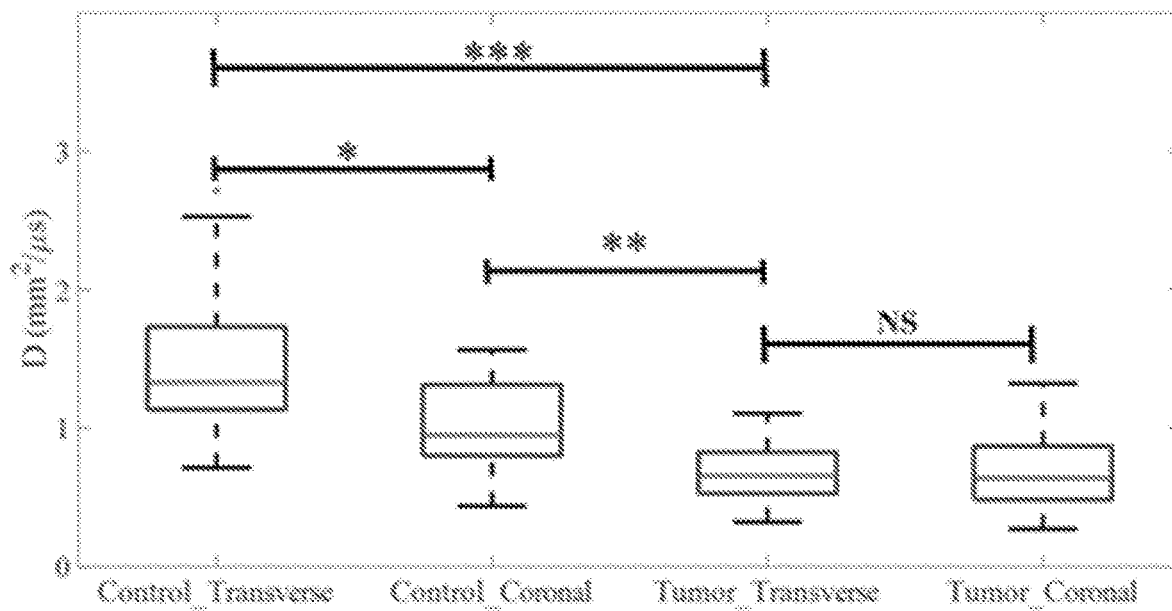
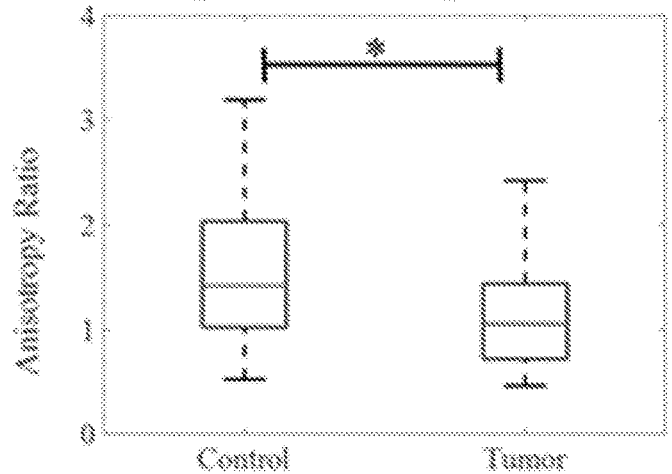
FIG. 13B

INTER-ELEMENT MATRIX IN ULTRASOUND CONTRAST AGENTS POPULATIONS TO MEASURE TRANSPORT PARAMETERS

CROSS-REFERENCE TO RELATED APPLICATIONS

This application is a national stage application filed under 35 U.S.C. 0 371 of PCT/US2018/062654 filed Nov. 27, 2018, which claims the benefit of U.S. provisional patent application No. 62/591,174, filed on Nov. 27, 2017, and entitled "INTER-ELEMENT MATRIX IN ULTRASOUND CONTRAST AGENTS POPULATIONS TO MEASURE TRANSPORT PARAMETERS," the disclosures of which are expressly incorporated herein by reference in their entireties.

STATEMENT REGARDING FEDERALLY FUNDED RESEARCH

This invention was made with government support under grant numbers CA165621, CA170665, and EB022311 awarded by the National Institutes of Health. The government has certain rights in the invention.

BACKGROUND

Tumors need to recruit new blood vessels to grow beyond a certain size, or to metastasize to other organs [1], and the structure of angiogenic, tumor-related vessels is abnormal. Contrary to the vasculature in healthy tissue, tumor vasculature is highly disorganized and isotropic [2], [3]. The vessels are tortuous with excessive branching and shunts[4]. It has been demonstrated that the microstructural properties of vascular networks, including micro-vessel density (MVD), and anisotropy, are useful parameters for distinguishing different types tumors [5]-[7]. Multiple studies have linked MVD [8]-[12] and vascular anisotropy to malignancy and overall prognosis. MVD has also been proved a significant and independent prognostic indicator[8], [13].

Biopsies are the current gold standard for the diagnosis of tumor malignancy. However, although a biopsy is highly specific, it is invasive in nature and is subject to selection bias [14]. Thus, there is a significant interest in developing non-invasive reliable methods to characterize the angiogenic microvasculature as a surrogate marker of malignancy. Various techniques including micro-CT [15] and optical frequency domain imaging [16] have been tested to characterize the microvasculature. Micro-CT scanning requires exposure to high intensity X-ray radiation, which is too high for clinical use, at the resolutions that would be required to visualize the microvasculature [17]. Optical coherence tomography (OCT) that can be used to visualize the vasculature with a very good spatial resolution (typically 1-20 micron) suffers due to insufficient penetration (2 mm) [18], [19] and very slow imaging speed [20]. Advanced optical coherence tomography technologies like Optical Frequency Domain Imaging (OFDI) can increase the acquisition speed but penetration depth is still limited compared to ultrasound and micro-CT [20]. Micro-MRI imaging has shown some potential in high resolution imaging of vasculature but it also suffers from very slow data acquisition speed [21].

Ultrasound is inexpensive compared to micro-CT and micro MRI and non-invasive. No exposure to ionizing radiation is required for ultrasound imaging as in case of micro-CT imaging. Ultrasound imaging has much higher tissue penetration depth compared to optical tomography. However, the conventional ultrasonic methods for cancer diagnosis lack specificity [22]. Methods relying on the use of ultrasound contrast agents have been developed for imaging the microvasculature [23], [24]. Development and use of ultrasound contrast agents has expanded over past 5 decades since it was first demonstrated that agitated saline could enhance the backscattered echoes by Gramiak and Shah in 1968 [25]. Use of CEUS for characterization of lesions in the kidney [26], prostate [27], breast [23][24], sentinel lymph nodes in breast cancer [30], pancreas [31] etc. has been demonstrated with varying degree of success over the past five decades. Acoustic angiography is a method relying on contrast agents that enables the 3D mapping of microvascular networks with a resolution down to 100-200 microns[32]-[34].

SUMMARY

An example method for measuring micro-architectural properties of vascular networks is described herein. The method can include injecting an ultrasound contrast agent into a medium, and transmitting a plurality of acoustic pulses into the medium using an ultrasound transducer array. Each respective acoustic pulse can be transmitted from a respective element of the ultrasound transducer array, or from a subset of elements of the ultrasound transducer array. The method can also include receiving a plurality of backscattered signals with the ultrasound transducer array in response to each respective acoustic pulse, and obtaining a response matrix including the backscattered signals. The method can further include extracting a coherent or incoherent contribution to the backscattered signals from the response matrix, and quantifying a property of a vascular network based on the coherent or incoherent contribution to the backscattered signals.

Additionally, the ultrasound contrast agent can include microbubbles. In some implementations, a concentration of the microbubbles can be less than about 0.5% ($5 \times 10^6$ microbubbles/mL) bubble concentration by volume. In some implementations, a concentration of the microbubbles can be between about 0.5% ($5 \times 10^6$ microbubbles/mL) and about 2% ($2 \times 10^7$ microbubbles/mL) bubble concentration by volume.

Alternatively or additionally, the backscattered signals can be received at every element of the ultrasound transducer array in response to each respective acoustic pulse. Alternatively, the backscattered signals can be received at a subset of elements of the ultrasound transducer array in response to each respective acoustic pulse.

Alternatively or additionally, the step of extracting the coherent or incoherent contribution to the backscattered signals can include determining a diffusion constant of the medium. For example, the incoherent contribution to the backscattered signals can be extracted from the response matrix, and the diffusion constant of the medium is related to the growth of a diffusive halo over time. Alternatively or additionally, the coherent contribution to the backscattered signals can be extracted from the response matrix, and the diffusion constant of the medium is related to the rate of shrinkage of a coherent intensity as a function of the transmitter-receiver distance over time. Optionally, the method can further include estimating a scattering mean free path using the diffusion constant of the medium. Optionally, the method can further include generating a map of the scattering mean free path over a dimension of a tumor.

Alternatively or additionally, the property of the vascular network can be a vessel density. In some implementations, the vessel density is the number of blood vessels per unit of tissue volume.

Alternatively or additionally, the property of the vascular network can be an anisotropy metric. For example, the anisotropy metric is related to respective scattering mean free paths for at least two orientations of the ultrasound transducer array. Optionally, the anisotropy metric is a ratio of the respective scattering mean free paths.

Alternatively or additionally, the ultrasound transducer array can be incorporated into a catheter.

Alternatively or additionally, the ultrasound transducer array can be incorporated into an ultrasound probe.

Alternatively or additionally, the acoustic pulses can have a frequency of between about 1 MHz and about 15 MHz. Optionally, the acoustic pulses can have a frequency of between about 8 MHz and about 10 MHz.

Alternatively or additionally, the method can optionally further include detecting or diagnosing a tumor based on the property of the vascular network.

Alternatively or additionally, the method can optionally further include detecting the presence of angiogenesis based on the property of the vascular network.

Alternatively or additionally, the vascular network can include a plurality of blood vessels, where a majority of the blood vessels of the vascular network have a dimeter less than 1 millimeter (mm).

An example method for detecting the presence or absence of a disease is also described herein. The method can include quantifying a property of a vascular network as described above. Additionally, the method can include capturing an ultrasound image of a tissue. The method can further include detecting the presence or absence of a disease in the tissue using the property of the vascular network in conjunction with the ultrasound image.

An example system for measuring micro-architectural properties of vascular networks is described herein. The system can include an ultrasound transducer array configured to transmit a plurality of acoustic pulses into a medium populated by an ultrasound contrast agent. Each respective acoustic pulse is transmitted from a respective element of the ultrasound transducer array, or by a subset of elements of the ultrasound transducer array. Additionally, the system can include a computing device including a processor and a memory operably coupled to the processor. The memory can have computer-executable instructions stored thereon that, when executed by the processor, cause the processor to receive a plurality of backscattered signals with the ultrasound transducer array in response to each respective acoustic pulse, obtain a response matrix including the backscattered signals, extract a coherent or incoherent contribution to the backscattered signals from the response matrix, and quantify a property of a vascular network based on the coherent or incoherent contribution to the backscattered signals.

An example non-transitory computer-readable recording medium for measuring micro-architectural properties of vascular networks is described herein. The non-transitory computer-readable recording medium can have computer-executable instructions stored thereon that, when executed by a processor, cause the processor to receive a plurality of backscattered signals with a ultrasound transducer array in response to each of a plurality of acoustic pulses transmitted into a medium populated by an ultrasound contrast agent. Each respective acoustic pulse is transmitted from a respective element of the ultrasound transducer array or by a subset of elements of the ultrasound transducer array. The non-transitory computer-readable recording medium can have further computer-executable instructions stored thereon that, when executed by the processor, cause the processor to, obtain a response matrix including the backscattered signals, extract a coherent or incoherent contribution to the backscattered signals from the response matrix, and quantify a property of a vascular network based on the coherent or incoherent contribution to the backscattered signals.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 5 illustrates example operations for the iterative Fullwave simulation method described herein.

FIGS. 10A, 10B, and 10C are for bubble concentrations of 0.5%, 1%, and 2%, respectively. FIGS. 10D, 10E, and 10F are for bubble concentrations of 0.5%, 1%, and 2%, respectively.

FIG. 13A illustrates the comparison of the diffusion constant (D) measured along both perpendicular orientations (e.g., transverse and coronal) for Control and Tumor. FIG. 13B illustrates the resulting anisotropy ratios of the averaged D values.

DETAILED DESCRIPTION

Figure 1:
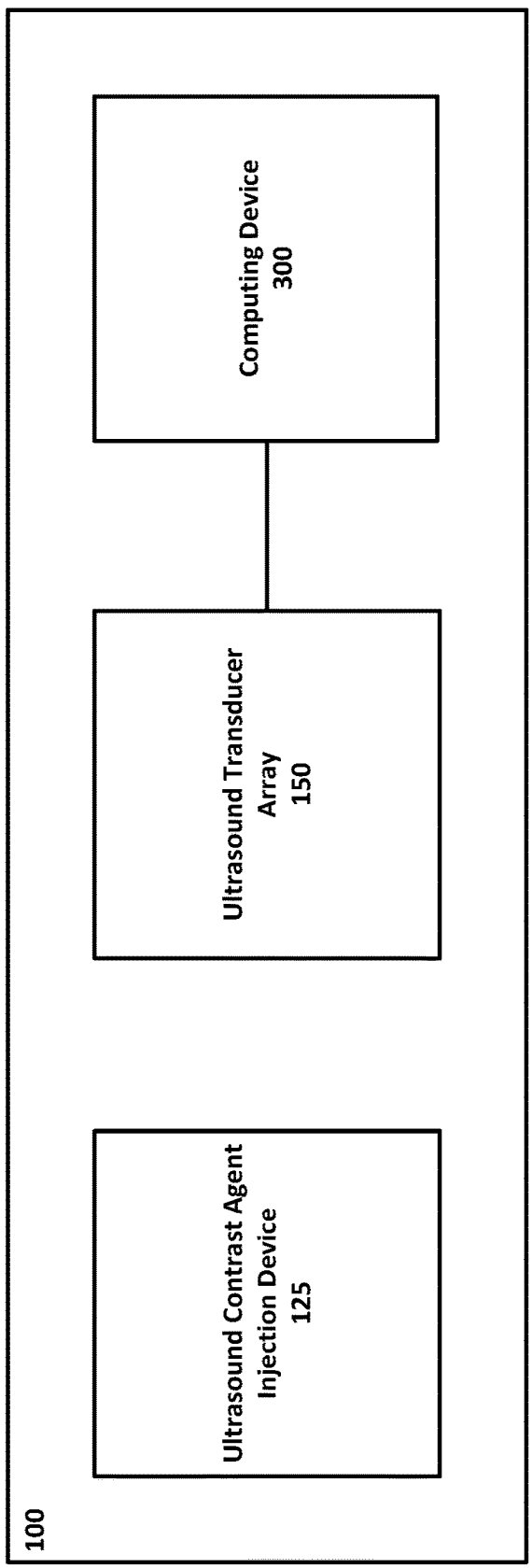
FIG. 1 is a block diagram illustrating an example system for measuring micro-architectural properties of a vascular network according to an implementation described herein.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subse- quently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for measuring micro-architectural properties of vascular networks, it will become evident to those skilled in the art that the implementations are not limited thereto. Additionally, this disclosure contemplates that the techniques for quantification of vascular microarchitectural properties can optionally be used in combination with contrast enhanced imaging modalities (e.g., acoustic angiography) to monitor disease progression (e.g., a tumor's response to treatment).

The principle of the technique described herein is to induce multiple scattering of ultrasonic waves by ultrasound contrast agents (e.g., microbubbles) in vascular networks. Multiple scattering is undesirable for imaging, but can be taken advantage of to extract wave transport parameters that are characteristic of the microarchitecture of the population of scatterers. A conventional ultrasound linear array is used herein in an unconventional fashion. Instead of doing beamforming and conventional imaging, ultrasound pulses are transmitted in the megahertz (MHz) range (e.g., 8 or 10 MHz), by firing individual elements of the array one-by-one, and receiving the backscattered signals on each element separately. Doing so, an inter-elemental matrix or inter-elemental-response matrix (e.g., response matrix) is acquired, which can be used to extract the coherent or incoherent contribution to the backscattered signals. For example, in some implementations, the incoherent contribution is extracted. The incoherent intensity grows over time as a diffusive halo and its width is determined by the diffusion constant (D) of the medium. From the diffusion constant, transport parameters such as the scattering and transport mean free path can be extracted. The Diffusion Constant can also be extracted from the profile of the coherent intensity as a function of the transmitter-receiver distance and time.

In contrast to conventional techniques, the technique described herein uses a medium populated by a distribution of ultrasound contrast agents (e.g., microbubbles) with a very low concentration, which are circulated in the medium (e.g., blood) flow. This allows measurement of micro-architectural properties of microvascular networks, such as the vessel density, which is a very good indicator of the invasiveness of a tumor, because the architecture of angiogenesis is different in healthy and tumoral tissues. Optionally, when the ultrasound probe is rotated over the vascular network, the transport and scattering mean free paths can be measured in various directions. This enables the assessment of the anisotropy of the vascular network, which is another marker of the tumor invasiveness. Although applications are described herein with regard to tumor/cancer analysis, it should be understood that the technique described herein can be for other applications, such as the diagnosis of atherosclerosis (e.g., through the characterization of the vasa vasorum), the study of kidney disease, the study of placental tissue, etc. This disclosure contemplates using the technique described herein to provide information when the architecture of the vascular network serves as a biomarker. In the examples described herein, only one frequency has been used to receive and transmit. It should be understood that combining low and high frequency, in order to increase the contrast to tissue ratio (e.g., transmit at 6 MHz and receive at 30 MHz), can be used with the technique described herein. It should be understood that the example frequencies for the dual frequency technique are provided only as examples and may have other values including, but not limited to, transmit at 6 MHz and receive at 18 MHz.

The technique described herein facilitates quantifying properties of vascular networks non-invasively, with an excellent resolution. However, no image is created. High resolution X-Ray or computed tomography (CT) provides images of vascular networks but i) it is a ionizing technique, not suited for the monitoring of treatment and ii) off line image processing is required to extract the parameters once the image has been created.

Acoustic angiography (AA) also provides images of the microvasculature with a high resolution. However, i) it is much slower than the technique presented here, ii) off line image processing is required to extract the parameters once the image has been created, and iii) the resolution of acoustic angiography enables the measurement of distances between vessels larger than the ones measured with the technique described herein.

The technique described herein is faster than CT and acoustic angiography. It does not provide an image, but it directly and non-invasively provides a quantitative parameter relevant for the assessment of malignancy. Because it is non-invasive, the technique is suited for treatment monitoring during chemotherapy, for example.

Referring now to FIG. 1, an example system 100 for measuring micro-architectural properties of a vascular network is shown. The system 100 can include an ultrasound contrast agent injection device 125, an ultrasound transducer array 150, and a computing device 300. The system 100 can also include acquisition circuitry (e.g., data acquisition, digitizer, signal conditioning, etc. hardware and/or software). As shown in FIG. 1, the ultrasound transducer array 150 and computing device 300 can be operably coupled using a communication link. This disclosure contemplates the communication link is any suitable communication link. For example, a communication link may be implemented by any medium that facilitates data exchange between the ultrasound transducer array 150 and computing device 300 including, but not limited to, wired, wireless and optical links. Example communication links include, but are not limited to, a LAN, a WAN, a MAN, Ethernet, the Internet, or any other wired or wireless link such as WiFi, WiMax, 3G or 4G.

The ultrasound contrast agent injection device 125 can be used to inject ultrasound contrast agent (e.g., microbubbles) into the medium. This disclosure contemplates using lipid shelled microbubbles as described herein. It should be understood that the ultrasound contrast agent is not intended to be limited to microbubbles and/or lipid shelled microbubbles, which are provided only as examples. As described herein, the microbubble concentration is relatively low. For example, a concentration of the microbubbles is optionally less than about 0.5% ($5 \times 10^6$ microbubbles/mL) bubble concentration by volume. Alternatively, a concentration of the microbubbles is optionally between about 0.5% ($5 \times 10^6$ microbubbles/mL) and about 2% ($2 \times 10^7$ microbubbles/mL) bubble concentration by volume. Alternatively, a concentration of the microbubbles is optionally up to about 5% bubble concentration by volume. Alternatively, a concentration of the microbubbles is optionally up to about 20% bubble concentration by volume. This disclosure contemplates using concentrations other than those described herein, which are provided only as examples.

The ultrasound transducer array 150 is optionally a linear transducer array. In some implementations, the ultrasound transducer array 150 is incorporated into a catheter, for example, the system 100 can include an intravascular ultrasound device for use diagnosing atherosclerosis. In other implementations, the ultrasound transducer array 150 is incorporated into an ultrasound probe. For example, a 128-element ultrasound transducer array L11-4v from VERASONICS of Seattle, Wash. is used in examples described herein. This disclosure contemplates using ultrasound transducer arrays other than those provided herein as examples, including two-dimensional (2D or 2-D), curved, and circular transducers. The ultrasound transducer array 150 can be configured to transmit a plurality of acoustic pulses into the medium populated by an ultrasound contrast agent (e.g., microbubbles). Each respective acoustic pulse is transmitted from one or more elements of the ultrasound transducer array. In some implementations, each respective acoustic pulse is transmitted from a respective element of the ultrasound transducer array. In other words, the ultrasound transducer array 150 transmits acoustic pulses one-by-one. In other implementations, each respective acoustic pulse is transmitted from two or more elements of the ultrasound transducer array, e.g., a few elements at a time. This can be done to increase signal-to-noise ratio. Optionally, the acoustic pulses have a frequency of between about 8 MHz and about 10 MHz. Optionally, the acoustic pulses have a frequency of between about 1 MHz and about 15 MHz. Optionally, the acoustic pulses have a frequency of between about 1 MHz and about 40 MHz. This disclosure contemplates using transmission frequencies other than those described herein, which are provided only as examples.

The backscattered signals in response to each respective acoustic pulse can be detected using the ultrasound transducer array 150. In some implementations, the backscattered signals are received at every element (i.e., all elements) of the ultrasound transducer array 150. In other implementations, the backscattered signals are received at a subset of elements (i.e., less than all elements) of the ultrasound transducer array 150. As described below, the computing device 300 can be configured to receive the backscattered signals, obtain a response matrix (e.g., an inter-elemental matrix or inter-elemental-response matrix (IRM) in some examples) including the backscattered signals, extract a coherent or incoherent contribution to the backscattered signals from the response matrix, and quantify a property of a vascular network based on the coherent or incoherent contribution to the backscattered signals.

It should be appreciated that the logical operations described herein with respect to the various figures may be implemented (1) as a sequence of computer implemented acts or program modules (i.e., software) running on a computing device (e.g., the computing device described in FIG. 3), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 2:
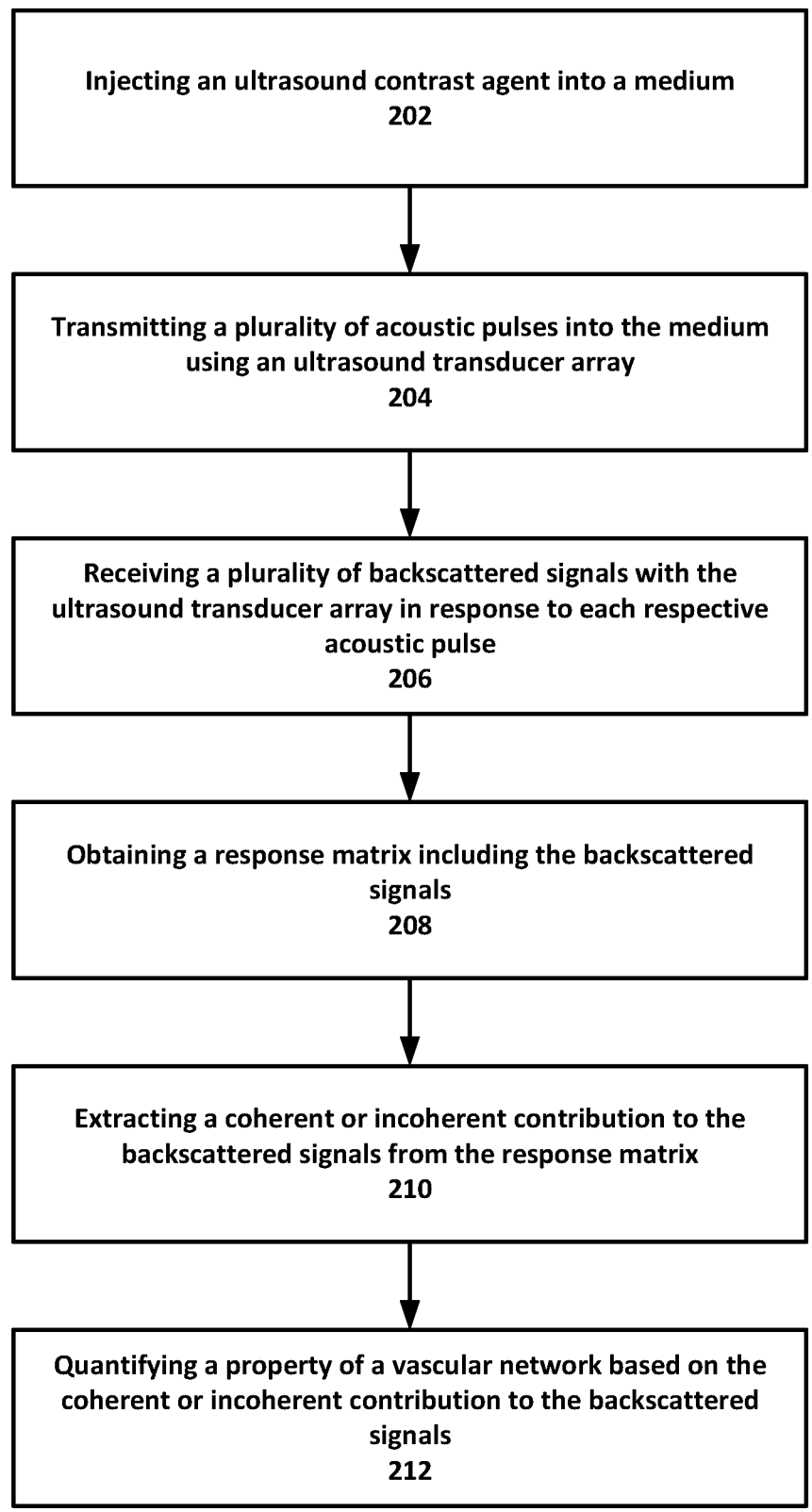
FIG. 2 is a flow diagram illustrating an example method for measuring micro-architectural properties of a vascular network according to an implementation described herein.

Referring now to FIG. 2, a flow chart illustrating example operations for measuring micro-architectural properties of a vascular network is shown. This disclosure contemplates that the technique described with regard to FIG. 2 can optionally be used on a vascular network including relatively small blood vessels. It should be understood that small blood vessels (e.g., diameter less than 1 mm) are difficult to detect, and in some cases undetectable, using traditional ultrasound techniques. For example, the vascular network can include a plurality of blood vessels where a majority of the blood vessels have a diameter less than 1 mm (e.g., the majority of the blood vessels are small blood vessels). At 202, an ultrasound contrast agent (e.g., microbubbles) is injected into a medium. For example, this disclosure contemplates using the ultrasound contrast agent injection device 125 of FIG. 1 to inject microbubbles into the medium. At 204, a plurality of acoustic pulses are transmitted into the medium using an ultrasound transducer array. For example, this disclosure contemplates using the ultrasound transducer array 150 of FIG. 1 to transmit the acoustic pulses. Each respective acoustic pulse can be transmitted from one or more elements of the ultrasound transducer array, e.g., acoustic pulses are transmitted individually one-by-one, or transmitted by two or more elements of the ultrasound transducer array. At 206, a plurality of backscattered signals are received with the ultrasound transducer array in response to each respective acoustic pulse. For example, this disclosure contemplates using the ultrasound transducer array 150 of FIG. 1 to receive the backscattered signals.

The backscattered signals can be transmitted from the ultrasound transducer array to a computing device (e.g., computing device 300 of FIG. 3) over a communication link as described above. Then, at 208, a response matrix including the backscattered signals is obtained. In some implementations, the response matrix is an inter-elemental matrix. At 210, a coherent or incoherent contribution to the backscattered signals is extracted from the response matrix. At 212, a property of a vascular network is quantified based on the coherent or incoherent contribution to the backscattered signals. As described herein, the property of the vascular network can serve as a biomarker. For example, in some implementations, a tumor can be detected or diagnosed based on the property of the vascular network. Alternatively or additionally, in some implementations, the presence of angiogenesis can be detected based on the property of the vascular network.

The step of extracting the coherent or incoherent contribution to the backscattered signals (e.g., step 210) can include determining a diffusion constant of the medium. For example, in some implementations, the incoherent contribution to the backscattered signals can be extracted from the response matrix. In this case, the diffusion constant of the medium is related to the growth of a diffusive halo over time. In particular, the width of the diffusive halo is determined by the diffusion constant of the medium. The growth of the diffusive halo can be determined by measuring the incoherent intensity as a function of time and of the transmitter-receiver distance. In other implementations, the coherent contribution to the backscattered signals can be extracted from the response matrix. In this case, the diffusion constant of the medium is related to the rate of shrinkage of the coherent intensity over time and over the transmitter-receiver distance. In particular, the width of the coherent intensity as a function of transmitter-receiver distance is inversely proportional to a square root of the diffusion constant of the medium.

In some implementations, the property of the vascular network is a vessel density. The vessel density is related to a scattering mean free path. Scattering mean from path can be determined using the response matrix. Techniques for estimating (e.g., simulating) scattering mean free path are described in the examples below. In some implementations, the vessel density is the number of blood vessels per unit of tissue volume. Alternatively or additionally, the property of the vascular network is an anisotropy metric. The anisotropy metric is related to respective scattering mean free paths for at least two orientations of the ultrasound transducer array. To obtain these measures, the ultrasound probe can be moved to at least two different orientations. For example, the two orientations can optionally be the transverse plane and the coronal plane as described in the examples below. The anisotropy metric is a ratio of the respective scattering mean free paths. If the ratio is 1 or close to 1, then the vascular network is isotropic. On the other hand, if the ratio is less or greater than 1, then the vascular network is anisotropic. Additionally, the relative value of the ratio provides a measure of the amount of anisotropy of the vascular network.

The technique described with regard to FIG. 2 does not require ultrasound imaging to quantify the property of the vascular network. This disclosure contemplates using the technique described with regard to FIG. 2 in conjunction with ultrasound imaging to detect the presence of disease in tissue. For example, the property of the vascular network can be quantified as described above in steps 202-212 of FIG. 2. Additionally, an ultrasound image of the tissue can optionally be captured. This disclosure contemplates that the ultrasound image can be captured using the same ultrasound transducer (e.g., ultrasound transducer 150 shown in FIG. 1) or a different ultrasound transducer than used for the operations of FIG. 2. The presence of the disease can be detected using both the property of the vascular network and the ultrasound image.

Figure 3:
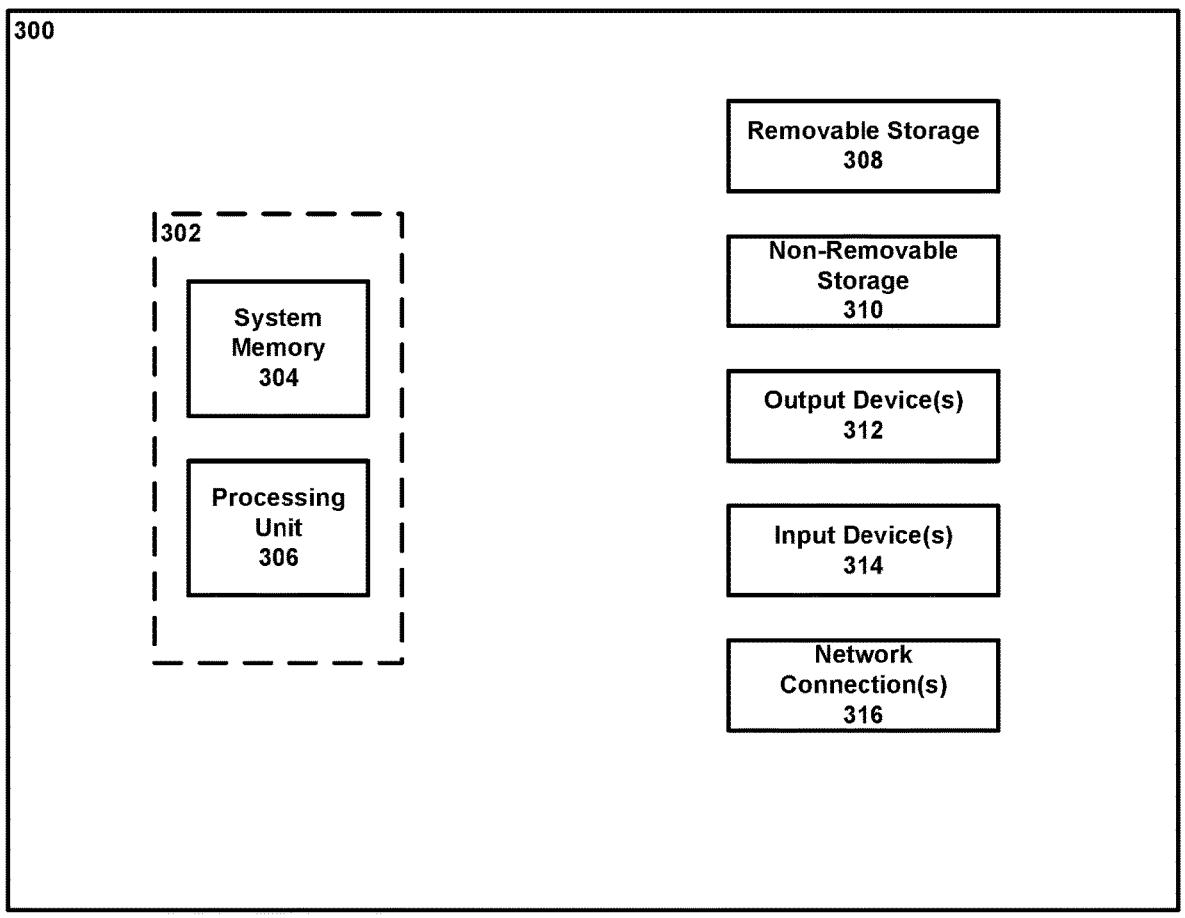
FIG. 3 is an example computing device.

Referring to FIG. 3, an example computing device 300 upon which embodiments of the invention may be implemented is illustrated. It should be understood that the example computing device 300 is only one example of a suitable computing environment upon which embodiments of the invention may be implemented. Optionally, the computing device 300 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 300 typically includes at least one processing unit 306 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 3 by dashed line 302. The processing unit 306 may be a standard programmable processor that performs arithmetic and logic operations necessary for operation of the computing device 300. The computing device 300 may also include a bus or other communication mechanism for communicating information among various components of the computing device 300.

Computing device 300 may have additional features/functionality. For example, computing device 300 may include additional storage such as removable storage 308 and non-removable storage 310 including, but not limited to, magnetic or optical disks or tapes. Computing device 300 may also contain network connection(s) 316 that allow the device to communicate with other devices. Computing device 300 may also have input device(s) 314 such as a keyboard, mouse, touch screen, etc. Output device(s) 312 such as a display, speakers, printer, etc. may also be included. The additional devices may be connected to the bus in order to facilitate communication of data among the components of the computing device 300. All these devices are well known in the art and need not be discussed at length here.

The processing unit 306 may be configured to execute program code encoded in tangible, computer-readable media. Tangible, computer-readable media refers to any media that is capable of providing data that causes the computing device 300 (i.e., a machine) to operate in a particular fashion. Various computer-readable media may be utilized to provide instructions to the processing unit 306 for execution. Example tangible, computer-readable media may include, but is not limited to, volatile media, non-volatile media, removable media and non-removable media implemented in any method or technology for storage of information such as computer readable instructions, data structures, program modules or other data. System memory 304, removable storage 308, and non-removable storage 310 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 306 may execute program code stored in the system memory 304. For example, the bus may carry data to the system memory 304, from which the processing unit 306 receives and executes instructions. The data received by the system memory 304 may optionally be stored on the removable storage 308 or the non-removable storage 310 before or after execution by the processing unit 306.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

EXAMPLES

Ultrasound contrast agents (UCA), such as microbubbles, enhance the scattering properties of blood, which is otherwise hypoechoic. The multiple scattering interactions of the acoustic field with UCA's are poorly understood due to the complexity of the multiple scattering theories and the nonlinear microbubble response. The majority of bubble models describe the behavior of UCA's as single, isolated microbubbles suspended in infinite medium. Multiple scattering models such as the Independent Scattering Approximation (ISA) can approximate phase velocity and attenuation for low scatterer volume fraction. However, all current models and simulation approaches only describe multiple scattering and nonlinear bubble dynamics separately. Described below is an approach (also referred to herein as the "iterative Fullwave simulation method") that combines two existing models: 1) a full-wave model that describes nonlinear propagation and scattering interactions in a heterogeneous attenuating medium and 2) a Paul-Sarkar model that describes the nonlinear interactions between an acoustic field and microbubbles. These two models were solved numerically and combined with an iterative approach. The convergence of this combined model was explored in silico for 0.5%, 1% and 2% bubble concentration by volume. The backscattering predicted by the iterative Fullwave simulation method was verified experimentally with water tank measurements performed with a 128-element linear array transducer. An excellent agreement in terms of the fundamental and harmonic acoustic fields is shown. Additionally, the iterative Fullwave simulation method correctly predicts the phase velocity and attenuation measured through transmission and predicted by the ISA.

Subsequent models proposed by Herring (Herring, 1941, Trilling, 1952), Keller-Miksis (Keller et al., 1956, Keller and Miksis, et al., 1980) and Prosperetti (Prosperetti, A., 1994) account for radiation damping. De Jong's model (de Jong et al., 1992, 1993, 1994a and 1994b) and Church's model (Crum et al., 1992, Church, C. C., 1995) are two fundamental models that account for the effects of encapsulation. De Jong's model assumes infinitesimal shell thickness whereas Church's model was derived to account for variations in shell thickness. Both these models assume that the liquid surrounding the bubble is incompressible. Recent models which include model by Morgan et al. (Morgan, K. E. et al., 2000), Hoff et al. (Hoff et al., 2000), Marmottant et al.

(Marmottant et al., 2005) and Maxwell et al. (Doinikov et al., 2007), consider the surrounding liquid as slightly compressible. A model proposed by Morgan et al. was the first model to require experimental determinations of unknown shell parameters. The Chatterjee-Sarkar Model (Chatterjee et al., 2003) predicts the response of lipid shelled microbubbles to low amplitude acoustic pulse.

All these models, including the Chatterjee-Sarkar Model, are based on curve fitting of the experimental observations. They assume a Newtonian behavior of the encapsulating shell. They can accurately predict the response of a microbubble to a low amplitude perturbation. The model used with the method described below was developed by Paul et al. (Paul et al., 2010) and is based on the Chatterjee-Sarkar Model. It describes the radial motion of the microbubble as follows:

$$R\ddot{R} + \frac{3}{2}\dot{R} = \frac{1}{\rho}\left[P_{G_0}\left(\frac{R_0}{R}\right)^{3\kappa}\left(1 - \frac{3\kappa \dot{R}}{c_0}\right) - 4\eta_L\frac{\dot{R}}{R} - P_0 - P_{ac}(t) - 4\kappa_s\frac{\dot{R}}{R^2} - \frac{2\sigma(R)}{R}\right]. \quad (1)$$

Here R(t) is the instantaneous radius of the bubble; $\rho$ is the equilibrium density of the surrounding liquid; $P_{G_0} = P_0 - P_v + 2\sigma/R_0$ is the equilibrium pressure inside the bubble; $R_0$ is the bubble radius at rest; $\kappa$ is the polytrophic exponent of the gas; $P_v$ is the vapor pressure inside the bubble; $\sigma$ is the surface tension for the liquid-gas interface; $\eta_L$ is the dynamic viscosity of the liquid; $P_0$ is the hydrostatic pressure in the liquid; and $P_{ac}(t)$ is the driving acoustic pressure. The choice of a polytrophic exponent is based on the Peclet number to account for thermal damping. The term $$4\eta_L\frac{\dot{R}}{R}$$

models damping from the viscosity of the surrounding liquid. $\kappa_S$ is the dilatational viscosity that accounts for the viscosity of the polymer shell. $\sigma(R)$ is a non-linear function of the bubble radius. It is given as follows:

$$\sigma(R) = \sigma_0 + \frac{E^S(R^2 - R_E^2)}{R_E^2}. \quad (2)$$

Here $E^S$ is the dilatational elasticity that accounts for the elastic behavior of the polymeric shell. $\sigma_0$ is the reference surface tension at unstrained position and $R_E$ is corresponding radius. This model (henceforth referred to as the Paul-Sarkar Model) accounts for compression only behavior observed with the microbubbles (Li, Q., 2013). It is valid for both small and large amplitude acoustic fields. Unlike previous models $E^S$ was not assumed to be constant. Rather, it was assumed to be a function of the relative change in surface area $E^S = E^S(\beta)$ where $\beta = dA/A = (R^2/R_E^2) - 1$. A is the surface area of the microbubble. Two models—the Quadratic Elasticity Model and the Exponential Elasticity Model—can be used for $E^S(\beta)$.

The Quadratic Elasticity Model (QEM):

$$E^S(\beta) = E_0^S - E_1^S\beta \text{ for } E_0^S - E_1^S\beta > 0 \quad (3)$$

$$E^S(\beta) = 0 \text{ for } E_0^S - E_1^S\beta > 0 \quad (4).$$

The Exponential Elasticity Model (EEM):

$$E^S(\beta) = E_0^S \exp(\alpha_s\beta) \quad (5).$$

Figure 4:
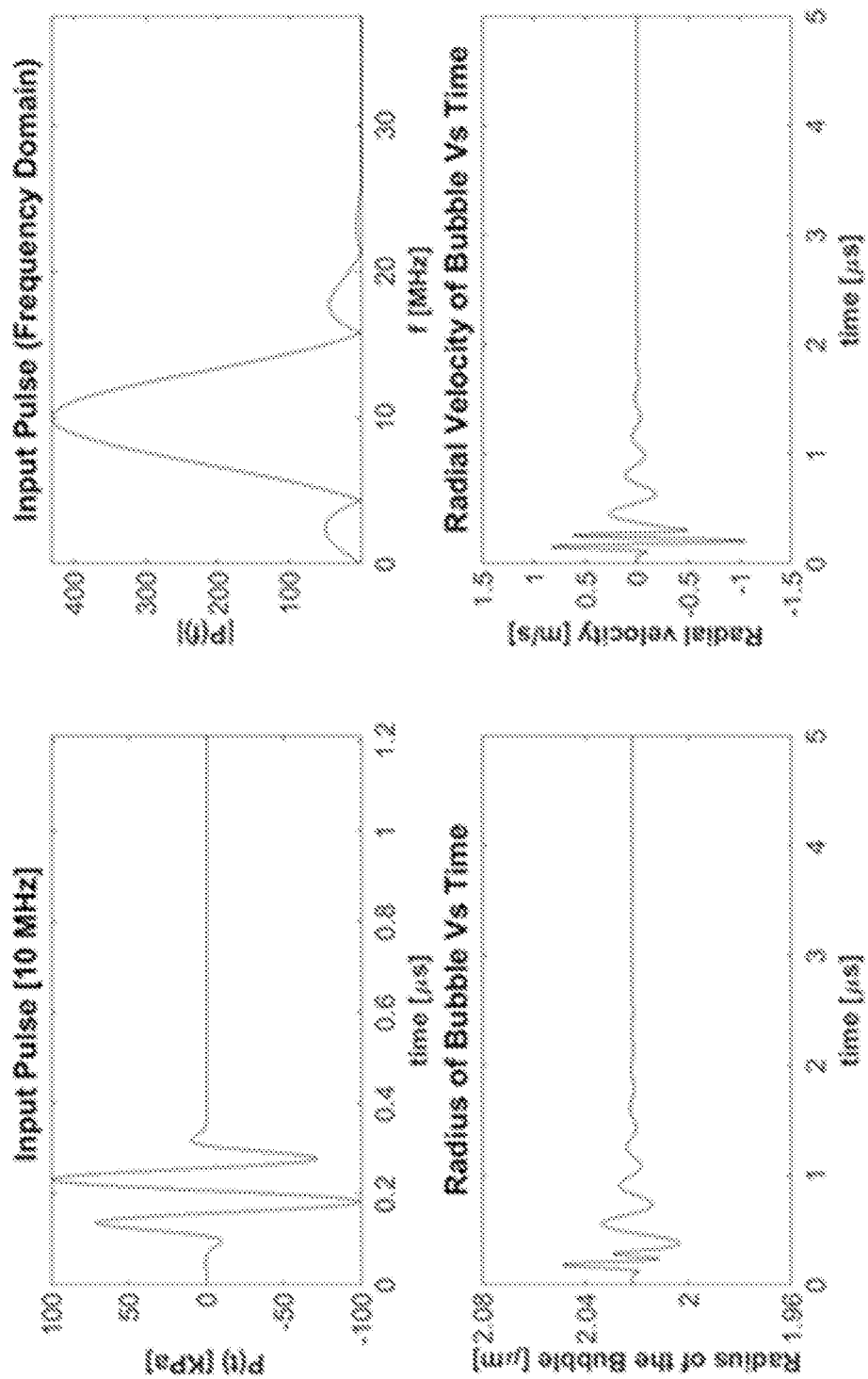
FIG. 4 illustrates bubble response according to Paul-Sarkar model (EEM) to a simple 10 MHz pulse.

The exponential elasticity model was used with the method described below because it is continuous and differentiable and it accurately describes compression only behavior of the microbubbles at high amplitude. Experimentally determined constants are $\alpha_s$ (decay constant) and $E_0^S$ (reference dilatational elasticity) for EEM and $E_0^S$ (reference dilatational elasticity) and $E_1^S$ (rate of change of dilatational elasticity with respect to relative change in surface area) for QEM. For a 10 MHz pulse, FIG. 4 shows the response of a 2-micron diameter microbubble. The constants used were $\sigma_0 = 0.02$ N/m, $E_0^S = 0.07$ N/m, $\alpha_S = 1.5$ and $\kappa_S = 7.5 \times 10^{-9}$ N-s/m and were obtained in the literature (Paul et al., 2013).

Knowing the radial displacement and radial acceleration, one can determine the scattered pressure from the bubble surface with the relation:

$$P_s(r, t) = \rho\frac{R}{r}\left(2\dot{R}^2 + R\ddot{R}\right). \quad (6)$$

These models describe the behavior of a single microbubble in an infinite homogeneous medium when subjected to an acoustic pulse. In general, the oscillations of a microbubble are non-linear in nature. It has already been demonstrated that significant multiple scattering can occur in a large population of bubbles (Stride, E. et al., 2005). Thus, in order to accurately simulate the wave propagation through a medium with randomly distributed microbubbles, it is necessary to account for non-linearity, multiple scattering and inhomogeneity.

Finite difference time domain methods have previously been used to solve three-dimensional (3D or 3-D) linear wave equations in inhomogeneous media (Mast, T. D. et al., 1997 and 2002). The non-linear wave equation has also been solved with finite differences but in a retarded time form and within the paraxial approximation that assumes that the field variations in the transverse direction are very slow compared to the field variations in the axial direction (Zabolotskaya, E. A., 1969). The full-wave equation does not rely on this approximation and describes the nonlinear propagation in a heterogeneous attenuating medium.

$$\nabla^2 p - \frac{1}{c_0^2}\frac{\partial^2 p}{\partial t^2} + \frac{\delta}{c_0^4}\frac{\partial^3 p}{\partial t^3} + \frac{\beta}{\rho c_0^4}\frac{\partial^2 p^2}{\partial t^2} + \frac{1}{\rho}\nabla p \cdot \nabla \rho - \sum_{m=1}^{v}\xi_m = 0 \quad (7)$$

Here, the first two terms represent the linear wave equation and the remaining three terms account for thermoviscous diffusivity, nonlinearity and relaxation respectively. The relaxation term $\xi_m$ should satisfy the equation:

$$\dot{\xi}_m + \omega_m\xi_m = a_m\omega_m\frac{\Delta c}{c_0}\nabla^2 p. \quad (8)$$

Here, p is the acoustic pressure, $c_0$ is the equilibrium sound speed, $\rho$ is the equilibrium density, $\delta$ is the acoustic diffusivity and $\beta$ is the non-linearity coefficient. Relaxation equation has v peaks at frequencies $\omega_m$. Weight $a_m$ depends upon frequency dependent upon the particular attenuation law modeled. Change in velocity $\Delta c$ must obey Kramers-Kronig relation to preserve causality. Detailed implementation of relaxation term is explained by Pinton et al. (Pinton, G. F. et al., 2009). The diffusivity is a function of the absorption coefficient α and the angular frequency ω as:

$$\delta = \frac{2\alpha c_0^3}{\omega^2}. \quad (9)$$

The full-wave equation accounts for medium nonlinearity, attenuation, and all wave effects, such as multiple scattering, reflection, and refraction. The full-wave equation was solved with the finite difference time domain method by Pinton et al. (Pinton, G. F. et al., 2009), which is referred to below as the Fullwave simulation tool. The advantage of using the full-wave equation is that it accurately describes an ultrasonic beam in the off-axis region and is valid for arbitrary scatterers in the field. Additionally, it is implemented in a way that it allows additive sources to be placed in the medium enabling any point of the domain to act as secondary acoustic source. It has been validated for long-range propagation such as in imaging (Pinton, G. F. et al., 2011).

The iterative Fullwave simulation method combines the Paul-Sarkar model describing the acoustic radiation by individual bubbles and the Fullwave simulation tool to model the interactions between the acoustic field and microbubbles during propagation through media containing a population of randomly distributed microbubbles.

Referring now to FIG. 5, using the iterative Fullwave simulation method, an acoustical map containing randomly distributed bubbles with a controlled volume fraction was generated. To ensure uniform distribution of microbubbles in the tubes, the computational grid was divided several sub-sections of 10×10 pixels and centers of microbubbles were randomly generated in each of these sub-sections. 1%, 2% and 0.5% distribution were generated by generating 1 microbubble per sub-section, 2 microbubbles per sub-section and 1 microbubble per 2 subsections (microbubbles were generated in 1 randomly selected subsection amongst two neighboring subsections) respectively. The homogeneous medium in which the microbubbles were distributed had the properties of water for all simulations described below. The iterative Fullwave simulation method first treats the bubbles as conventional (linear) scatterers in the $0^{th}$ iteration (e.g., as shown in FIG. 5). A 10 MHz 3-cycle Gaussian pulse with peak negative pressure of 600 kPa is transmitted in the medium. During this first step, the pressure at each bubble's surface is recorded. Then, using equations (3), (4) and (7) and using constants $\gamma_0$=0.02 N/m, $E_0^S$=0.07 N/m, $\alpha$=1.5 and $\kappa^S$=7.5×10$^{-9}$ N-s/m, the radial displacement of each microbubble is evaluated. The radiated pressure by each microbubble is evaluated using equation (6). In the $1^{st}$ iteration (e.g., as shown in FIG. 5), these pressure signals are included as additive sources at each bubble location and ultrasound propagation is again simulated just like in the $0^{th}$ iteration. Then, the pressure at each bubble's surface is recorded again. The same procedure is repeated over all the iterations (e.g., as shown in FIG. 5) to account for all multiple scattering interactions, and the additive source term is modified for every subsequent iteration. The corrected radiated pressure is evaluated for every iteration following the same procedure. This iterative approach facilitates accounting for multiple scattering interactions between microbubbles.

Figure 6A:
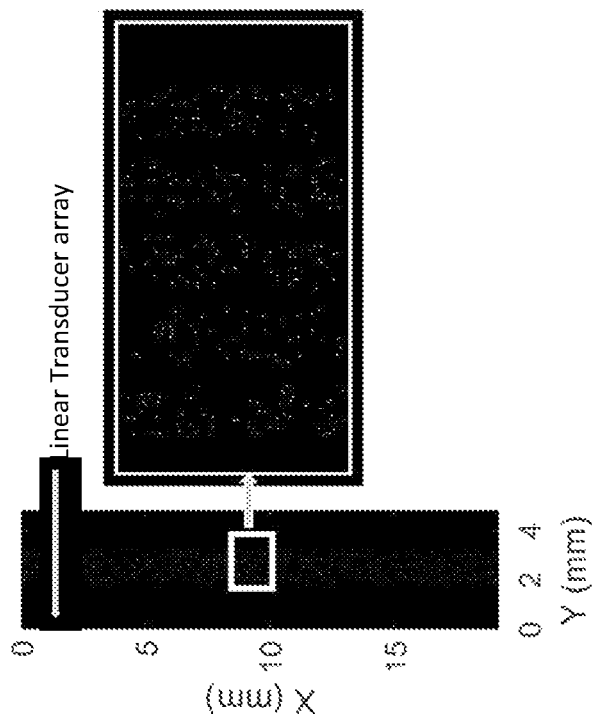
FIG. 6A illustrates the simulation setup according to an example described herein, which includes a 64-element linear array with five tubes separated by 250 microns (center-to-center) distance with grid step 2.13 micron.
Figure 7:
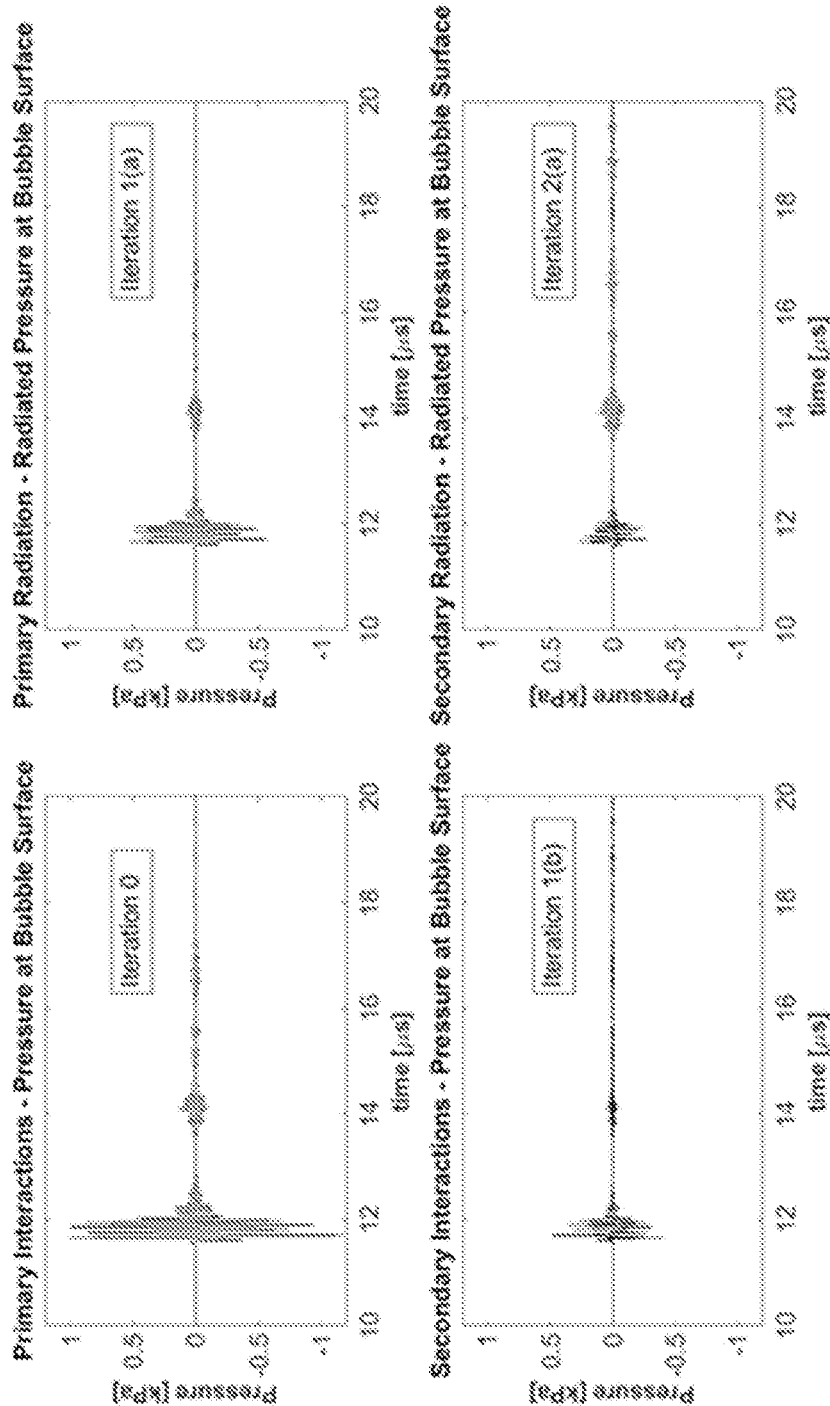
FIG. 7 illustrates primary and secondary interactions at one of the bubbles for backscattering simulation at 1% bubble concentration.

A set of 2-D simulations was conducted to model the backscattering of ultrasound by randomly distributed microbubbles in a set of acoustically transparent tubes. The simulation setup is shown in FIG. 6A. To validate the convergence of the iterative Fullwave simulation method, 20 iterations were carried out. An array of 64 elements was simulated. In each simulation, only one of the 64 elements was used to transmit an acoustic pulse with a central frequency of 10 MHz and all 64 transducer element were used to receive the backscattered signals. All of the elements of the array were consecutively used as transmitters one by one, until a 64×64×N matrix was obtained where N is number of time points. This matrix is referred to as the inter-elemental matrix or inter-elemental-response matrix (also referred to above as a "response matrix," for example with regard to FIGS. 1 and 2). The grid size used was 2.13 micron (90 points per wavelength) for these simulations. The simulations were conducted for 0.5% (5×10$^6$ microbubbles/ml), 1% (10$^7$ microbubbles/ml) and 2% (2×10$^7$ microbubbles/ml) bubble concentration by volume. These concentrations based on clinically relevant concentrations (Appis, A. W. et al., 2015). The width of each transducer element was 300 microns. The dimension of the medium was 19.2×4.8 mm. The width of each tube was 200 microns and the center-to-center distance between neighboring tubes was 250 microns. Perfectly matched layer (PML) boundary conditions were applied at all four boundary surfaces to avoid surface reflections. The incident acoustic pressure on one bubble in the medium, while simulating propagation of ultrasound through the media with 1% bubble concentration, and the corresponding scattered pressure from the bubble surface for Iteration #1 and Iteration #2 are shown in FIG. 7. After each iteration, the scattered pressure is evaluated at each bubble surface and it is used as a source term for the next iteration.

Figure 6B:
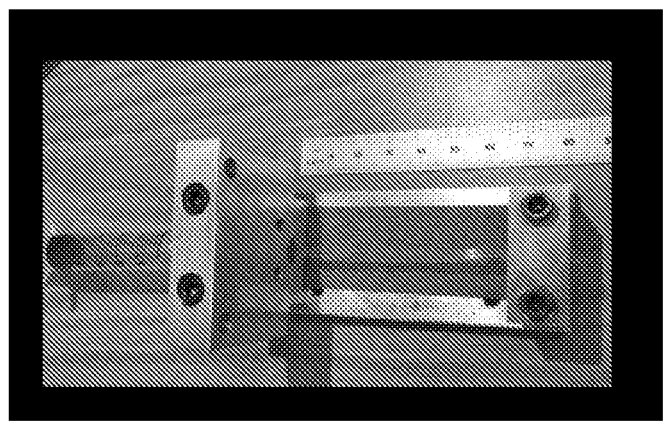
FIG. 6B illustrates the experimental setup according to an example described herein, where five 200-micron cellulose tubes are separated by a 250-micron center-to-center distance and into which microbubbles are injected using an attached syringe.

To validate the simulation results, a set of experiments replicating the simulations was conducted. To evaluate the accuracy with which the methods described herein can estimate the inter-elemental matrix, an experiment that mimics the simulation setup was conducted using a set of cellulose tubes of 200-micron diameter each with neighboring tubes separated by a distance of 250 microns. This setup is shown in FIG. 6B. As in the simulation, five tubes were used in the experiment. A 128-element linear transducer array (L11-4v, Verasonics, Seattle, Wash.), was used for this experiment. Bubbles were injected slowly in all tubes simultaneously using a single syringe to ensure they are equally distributed in the tubes. The data acquisition sequence described previously for the simulations was used in the experiments to acquire and inter-elemental matrix of dimensions 128×128×N.

Lipid shelled microbubbles were fabricated according to a method described by Streeter et al. (Streeter, J. E. et al., 2010). The experiment ensured that the population of microbubbles was approximately 2 μm in diameter to ensure consistency with the simulation by size sorting it using optical scattering (Accusizer 780A, PSS-NICOMP, Port Richey, Fla.). To compare the simulation and experimental results, only the data transmitted and collected by the central 64 elements of the linear array was used. The experimental data was resampled so that both datasets had the same time step.

To further validate the iterative Fullwave simulation method, the transmit of a plane wave through the medium was simulated to measure the phase velocity and attenuation coefficient. In a heterogeneous medium, when one of the components is highly compressible compared to the other (in this case, the microbubbles are significantly more compressible than the surrounding water), the resulting acoustic velocity is much lesser than the acoustic velocity in each of the individual media. This was first observed by Wood (Wood, A. B., 1955) while studying the transmission of acoustic signals through curtains of bubbles in water. Using Wood's theory, the velocity in the heterogeneous medium can be predicted:

$$c = \sqrt{\frac{E_f E_a}{[xE_f + (1-x)E_a][x\rho_a + (1-x)\rho_f]}}, \quad (10)$$

where c is velocity of sound, x is the volume fraction of air, $\rho_a$ and $\rho_f$ are densities of fluid and air respectively and $E_f$ and $E_a$ are bulk modulus of fluid and air respectively. However, Wood's theory does not to account for dispersion. Wood's theory gives reasonable estimate of velocity at low microbubble concentrations but it's not accurate in presence of significant multiple scattering. A validated approach to predict the velocity and attenuation of ultrasound is the Independent Scattering Approximation (ISA). To predict the velocity using the ISA, a reference simulation with no scatterers and another simulation with a single scatterer (bubble) was conducted to calculate the normalized forward scattering intensity. From this, the effective wave number for a given volume fraction of scatterers can be evaluated (Mézière et al., 2014), which gives access to the phase velocity and attenuation.

The detailed procedure to determine the velocity and attenuation using the ISA is described in Meziere et al (Mézière et al., 2014). As the emitted signal is a pulse centered at 10 MHz with a −6 dB bandwidth of around 100%, this study was limited to the 5-15 MHz frequency range. The transmitted signals were recorded for each simulation and experiment at various depths and by performing Fast Fourier Transforms (FFT) the signal was converted into the frequency domain, in which the phase velocity was calculated by unwrapping the phase angle $\varphi_\omega$ (z) of the frequency domain signal $s_\omega$ (z) as, $$\varphi(z) = \arg(s_\omega(z)) = \varphi(0) + kz \quad (11),$$

where z is the depth at which transducer was placed. The phase velocity can be calculated as follows:

$$v(\omega) = \frac{\omega}{k(\omega)}. \quad (12)$$

The attenuation coefficient $\alpha(\omega)$ can be computed by assuming an exponential decay as follows:

$$|s(\omega)| = e^{-\alpha(\omega)z} \quad (13).$$

Figure 8A:
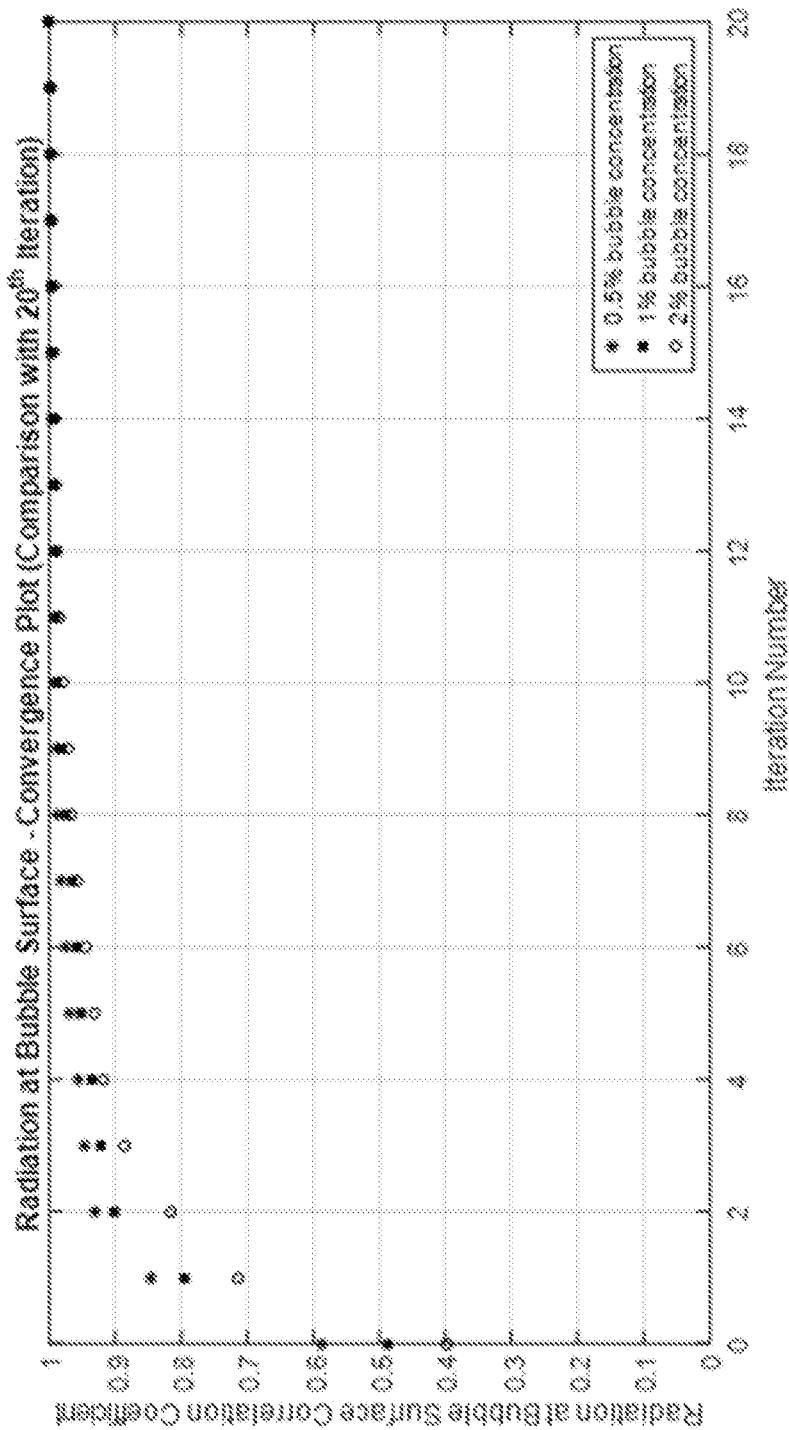
FIG. 8A illustrates a convergence plot for radiation at bubble surface.

After completing 20 iterations of the simulation, the correlation coefficients between the scattered pressure on the surface of a particular bubble for a particular iteration and the corresponding scattered pressure after the $20^{th}$ iteration were calculated. Averaging the correlation coefficients over all the bubbles for a particular iteration yields the average correlation coefficient for that particular iteration. The convergence plots for each of the simulations are shown in FIG. 8A. Within eight iterations, the correlation coefficient was higher than 0.99 for all simulations.

Figure 8B:
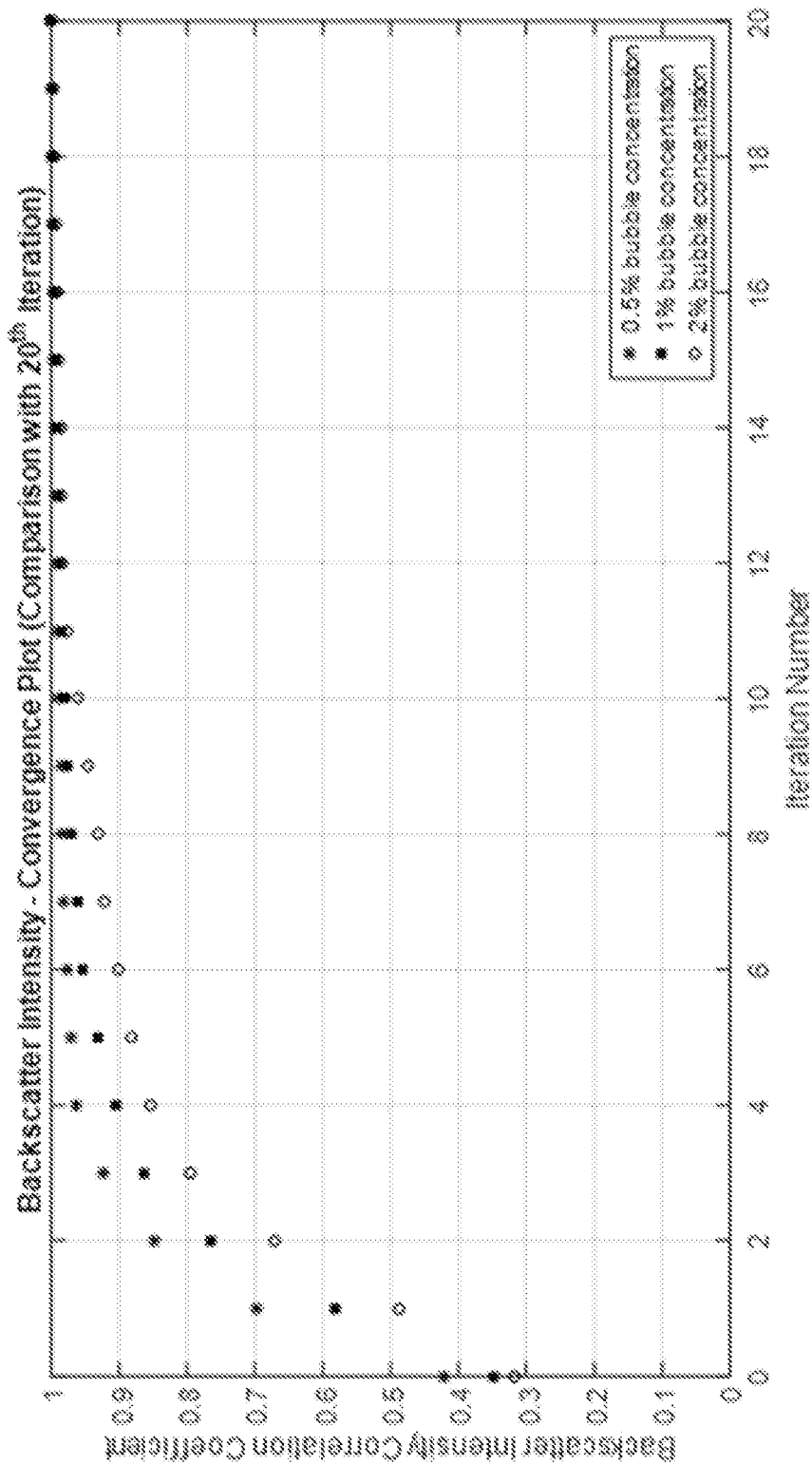
FIG. 8B illustrates a convergence plot for intensity of scattered signals.

Another way of assessing the convergence of the iterative Fullwave simulation method is to evaluate the convergence of the intensity of the pressure radiated by each bubble during a particular iteration compared to the $20^{th}$ iteration. FIG. 8B shows the convergence plot for the backscatter intensity of the pressure radiated by the microbubbles.

Figure 9:
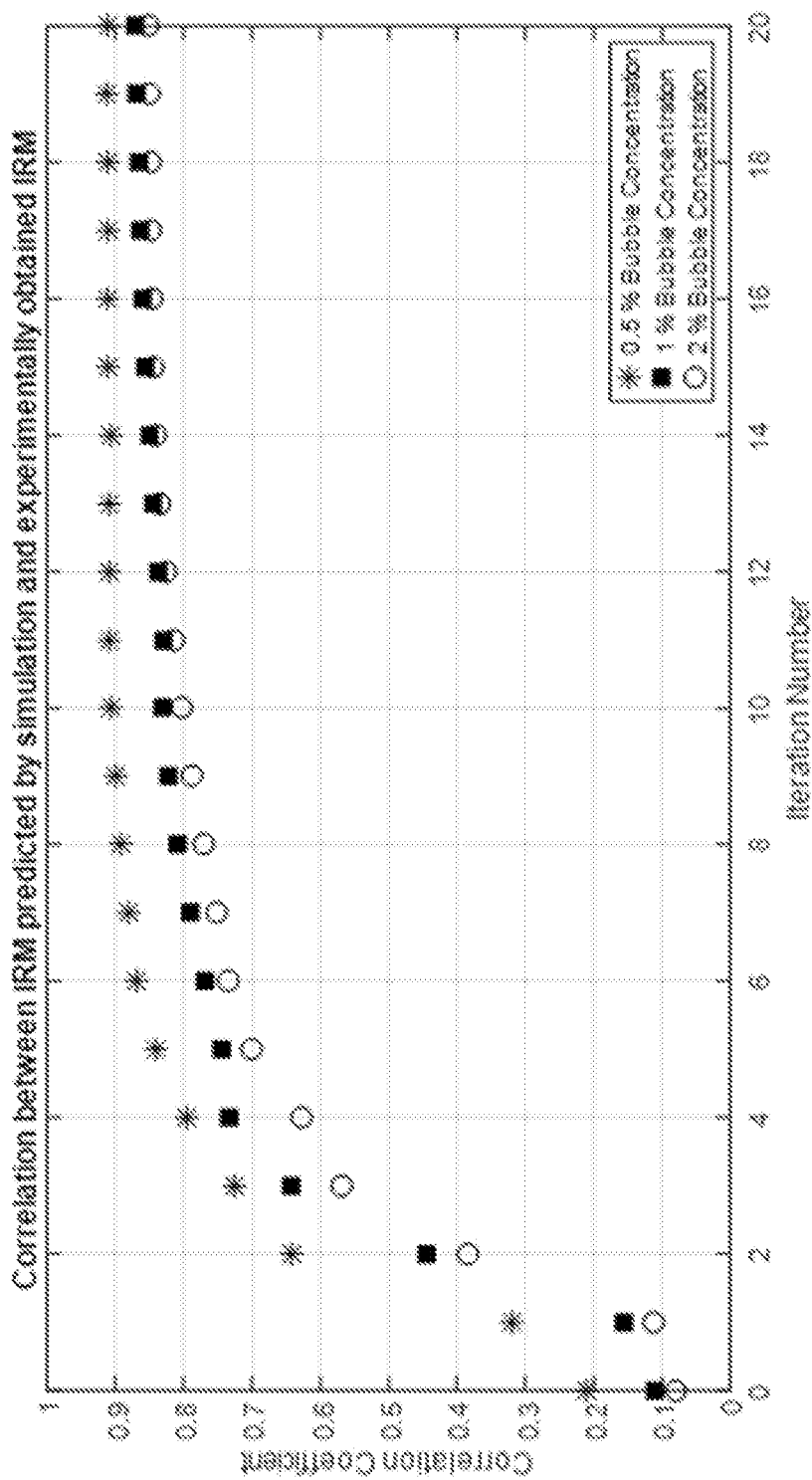
FIG. 9 illustrates the comparison between the experimentally obtained inter-elemental matrix and the inter-elemental matrix produced from simulations (e.g., using the iterative Fullwave simulation method).

The correlation coefficient between experimentally recorded inter-elemental matrix (IRM) and the computationally evaluated inter-elemental matrix (IRM) using the iterative Fullwave simulation method after each of the 20 iterations is shown in FIG. 9 for all bubble concentrations (0.5%, 1% and 2%).

The convergence plots shown in FIGS. 8A and 8B show that, at low concentrations (0.5% and 1%), 8 iterations are sufficient to simulate the multiple scattering interactions occurring between the micro-bubbles. For a 2% concentration however, a larger number of iterations (around 12) was required to reach a correlation coefficient of 0.99. This was expected, as an increase in the micro-bubble concentration leads to an increased number of scattering interactions. These results are confirmed by the correlation between the experimental and simulation results shown in FIG. 9. The lower the micro-bubble concentration, the sooner the experimental and simulation results will be in agreement. For a 0.5% concentration, a correlation coefficient of 0.9 between simulation and experiments is reached after four iterations. Eight and ten iterations are required to achieve the same agreement for 1% and 2% concentrations respectively.

Figure 10A:
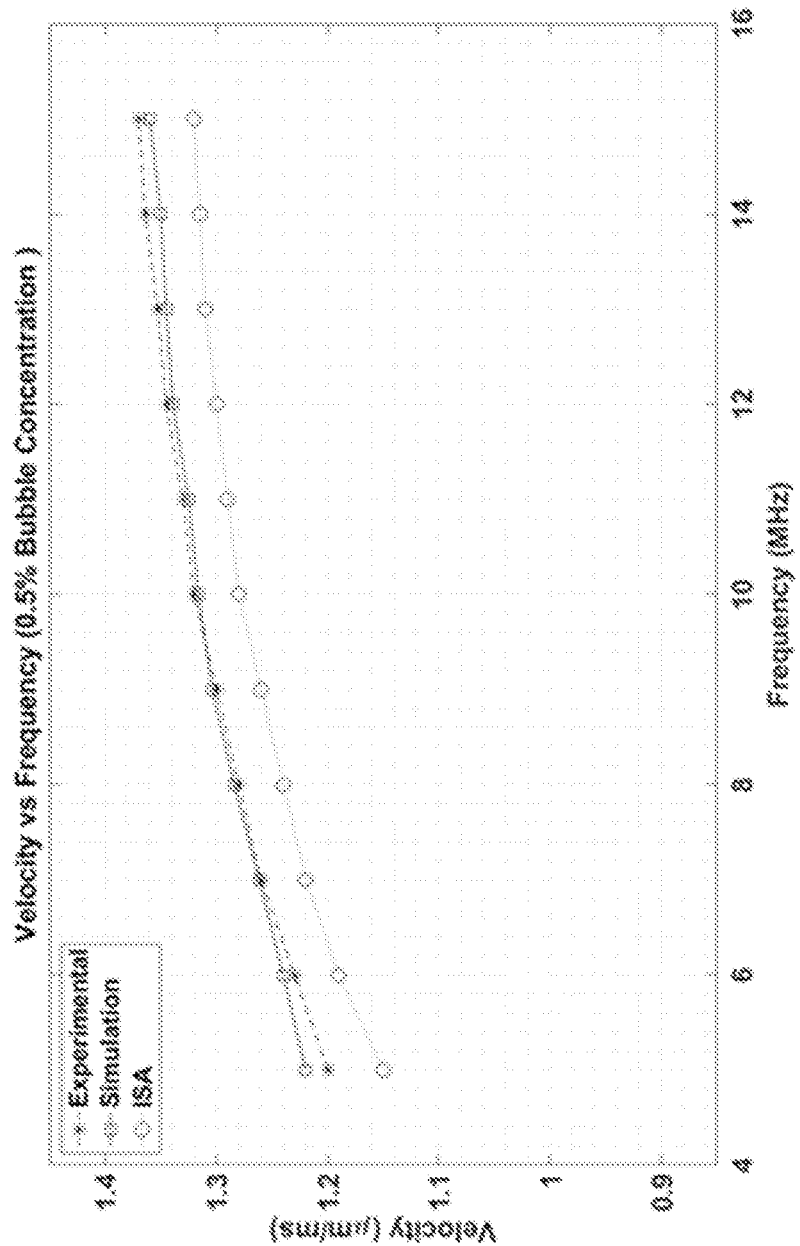
FIGS. 10A-10C illustrate the comparison between the phase velocity predicted by simulation (e.g., using the iterative Fullwave simulation method) and the phase velocity predicted by ISA approach. The experimentally measured phase velocity is also shown in FIGS. 10A-10C.
Figure 10B:
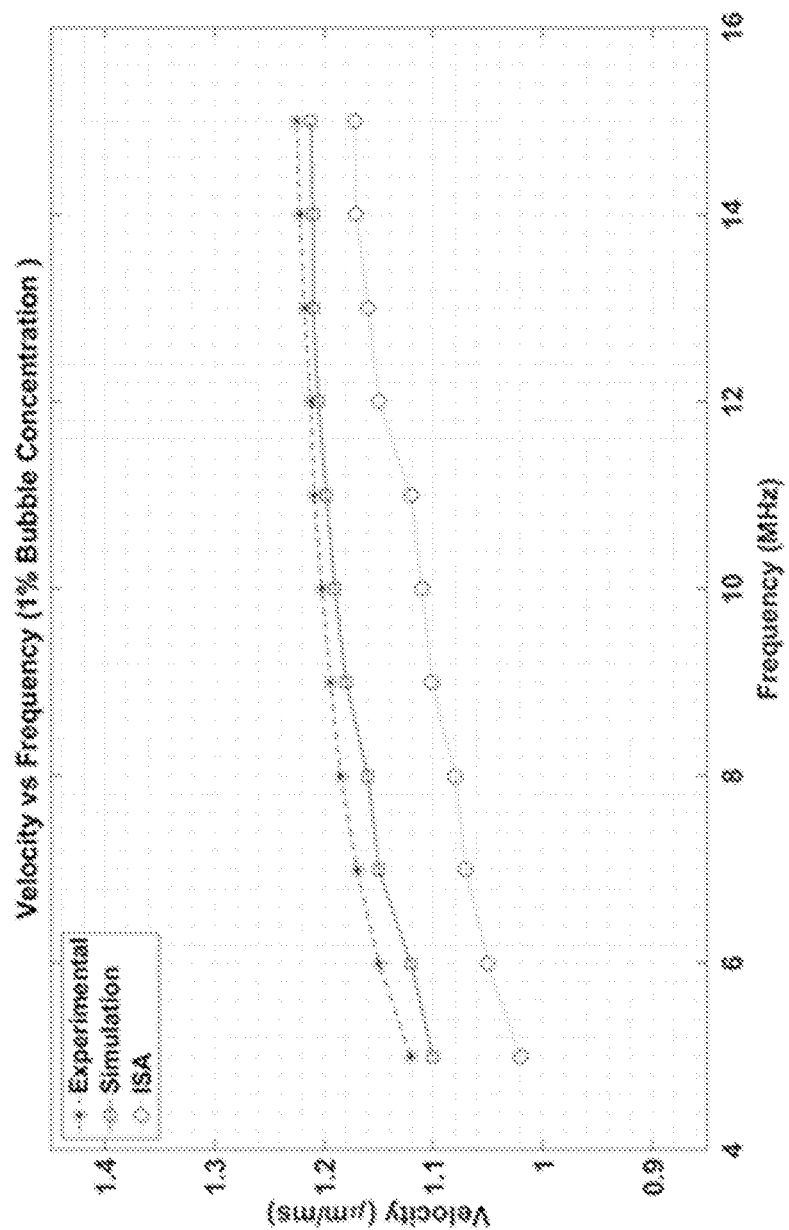
Figure 10C:
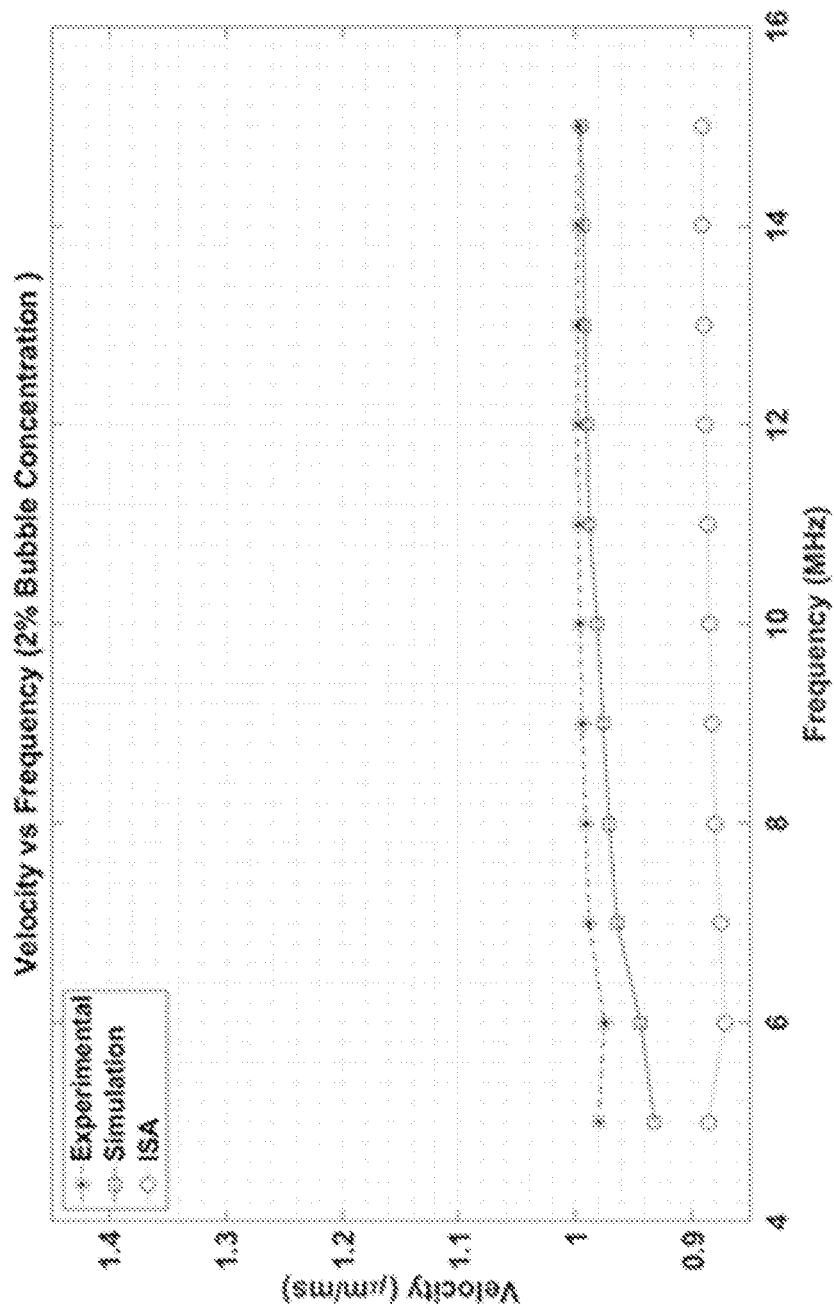
Figure 10D:
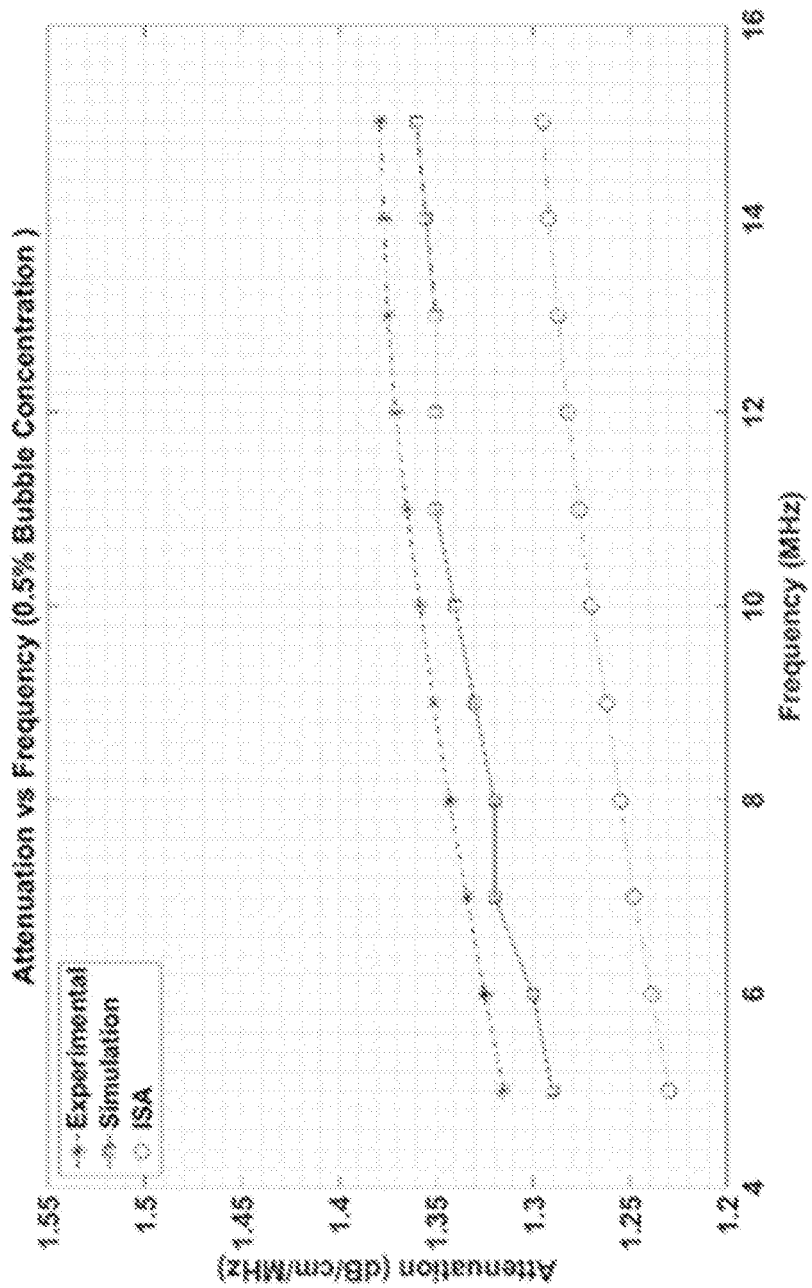
FIGS. 10D-10F illustrates the comparison between the predicted attenuation coefficients by simulation (e.g., using the iterative Fullwave simulation method) and the predicted attenuation coefficients by ISA approach. The experimentally measured attenuation coefficients are also shown in FIGS. 10D-10F.
Figure 10E:
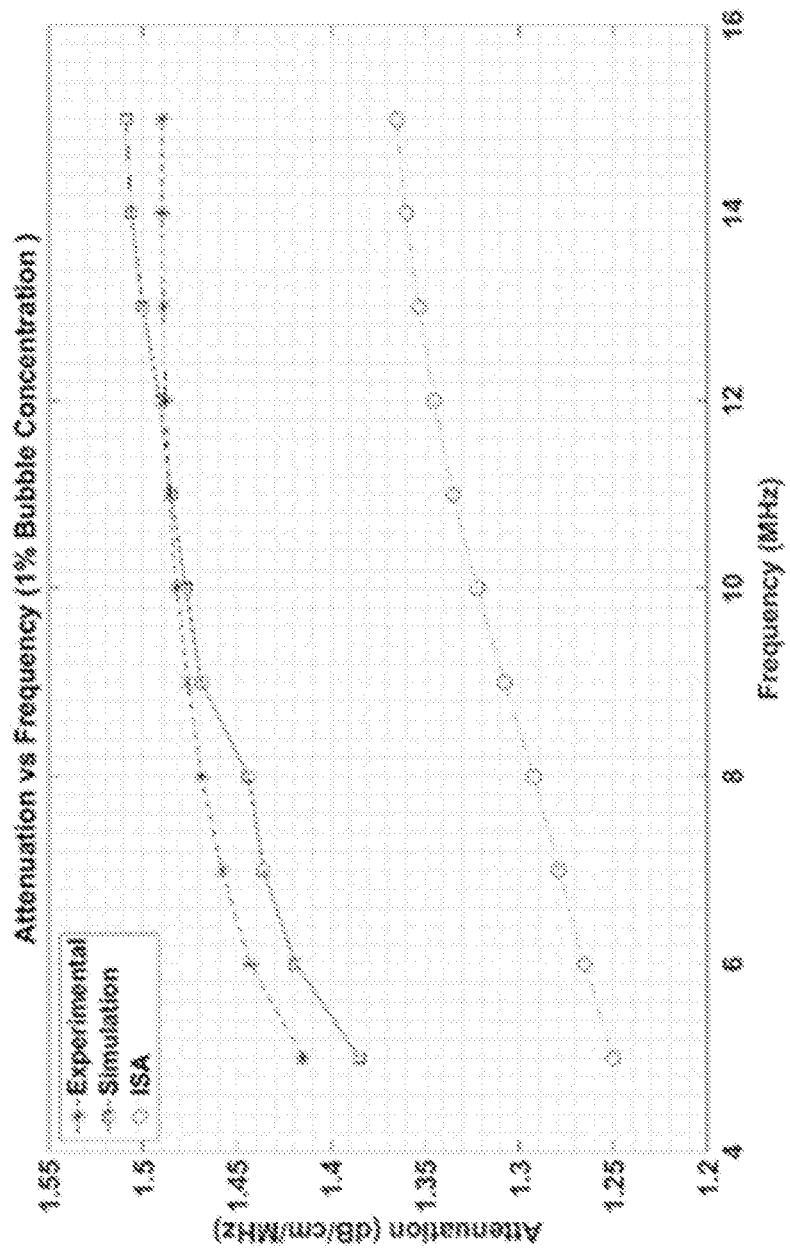
Figure 10F:
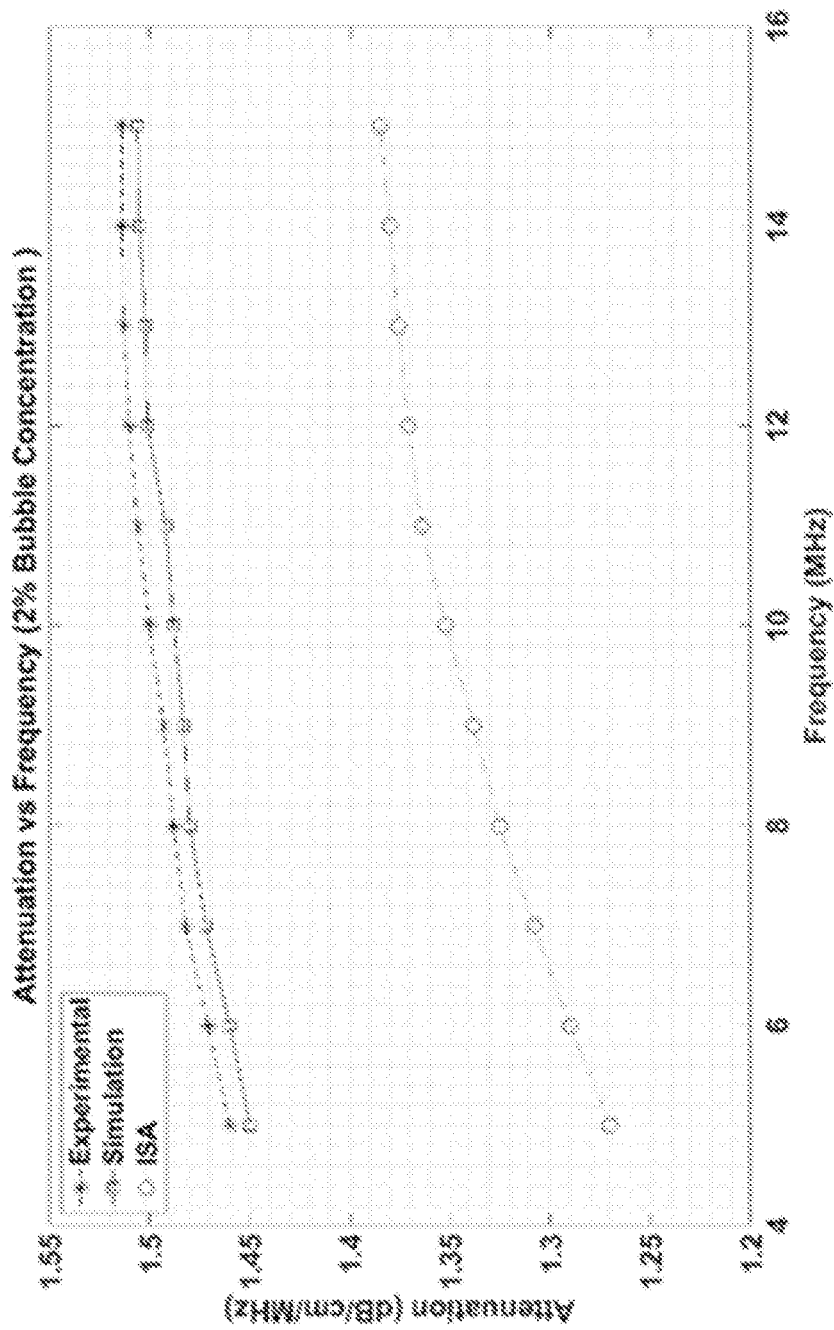

FIGS. 10A, 10B and 10C show a comparison between the velocities predicted by the iterative Fullwave simulation method ("Simulation"), measured from the experiments ("Experimental"), and predicted by the ISA ("ISA"). FIGS. 10D, 10E and 10F show a comparison between the attenuation coefficients predicted by the iterative Fullwave simulation method ("Simulation"), measured experimentally ("Experimental"), and predicted by the ISA ("ISA").

Figure 11A:
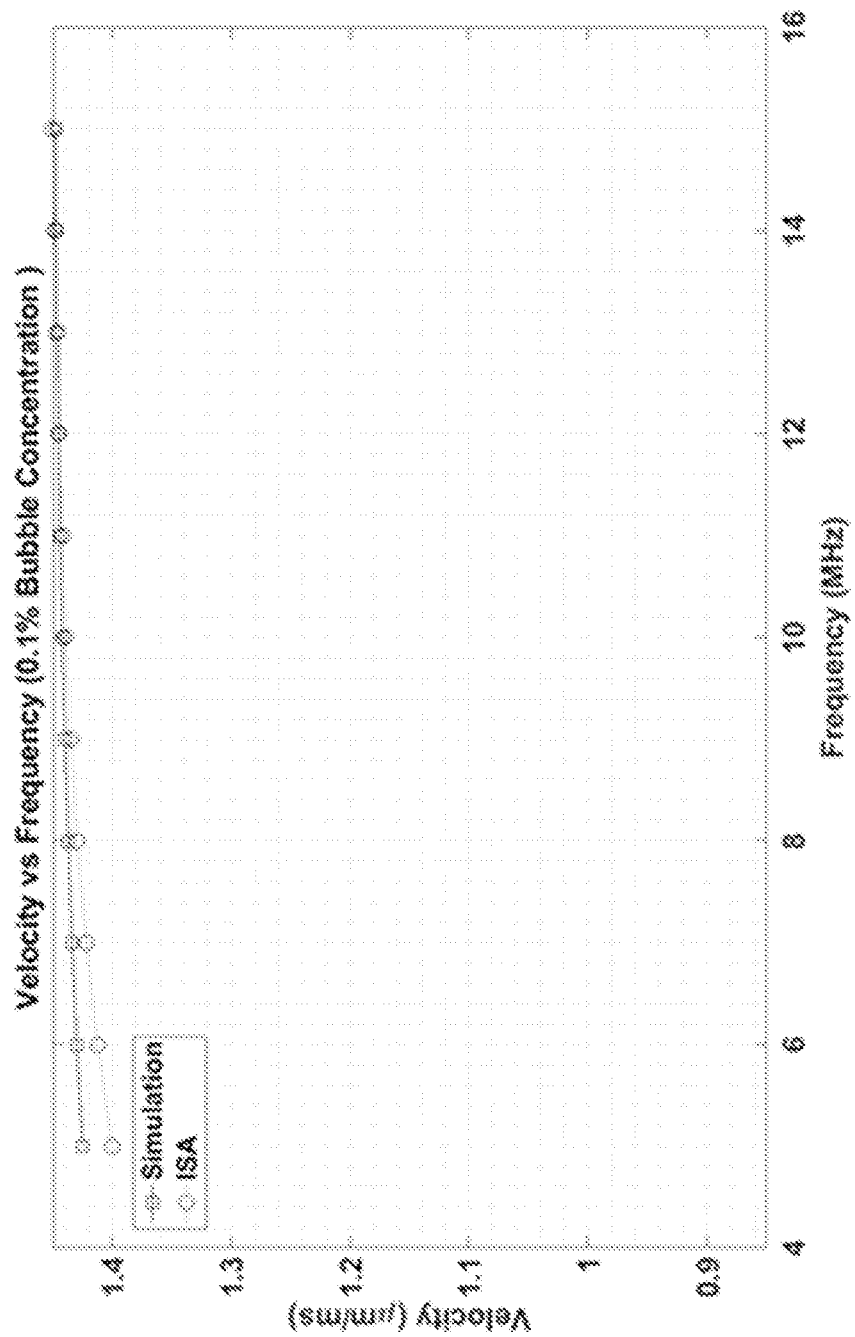
FIG. 11A illustrates the comparison between the phase velocity predicted by simulation (e.g., using the iterative Fullwave simulation method) and the phase velocity predicted by ISA approach.
Figure 11B:
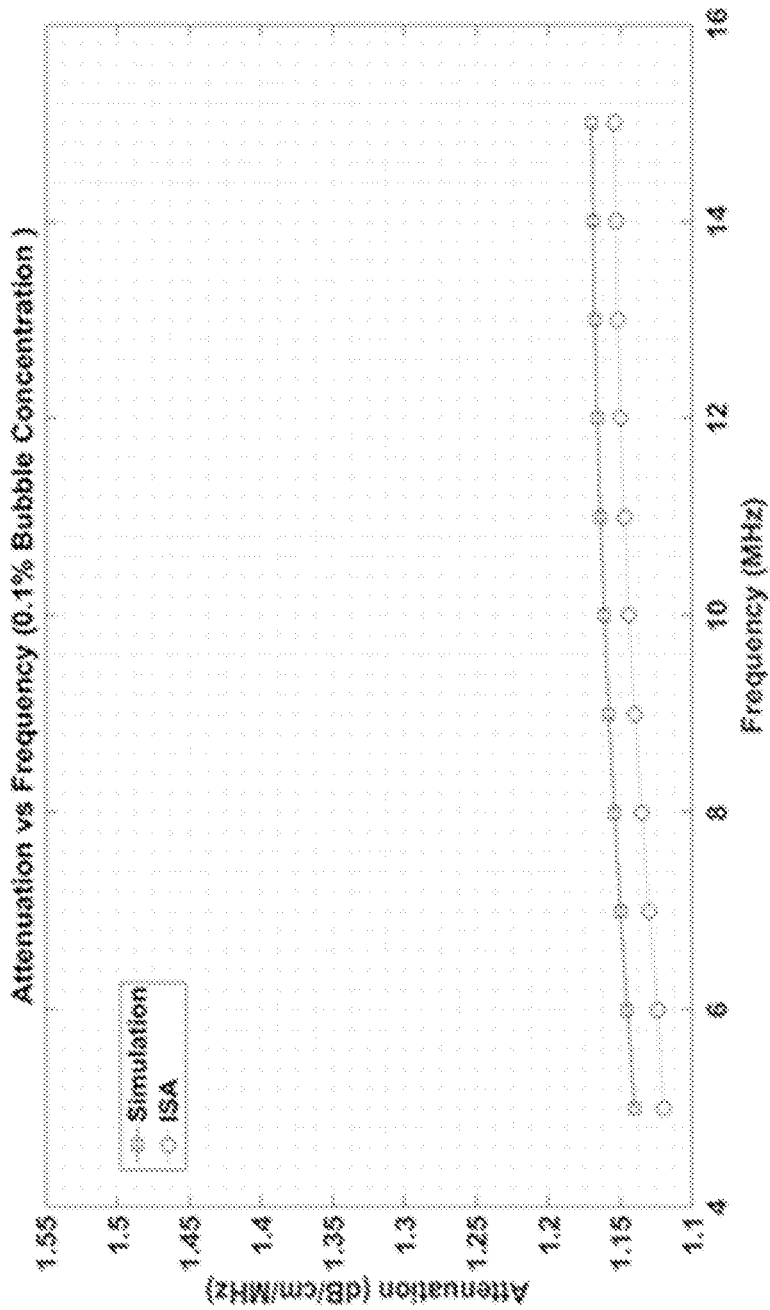
FIG. 11B illustrates the comparison between predicted attenuation coefficients by simulation (e.g., using the iterative Fullwave simulation method) and the predicted attenuation coefficients by ISA approach.

FIGS. 10A-10F show overall a very good agreement between the simulation results (e.g., using the iterative Fullwave simulation method) and the experimental results for all concentrations, both in terms of the velocity and the attenuation. As expected, the ISA predictions of the phase velocity and attenuation are more accurate for lower concentrations although the attenuation remains underestimated. This is due to the fact that the ISA only accounts for the first order interactions between the micro-bubbles, and does not allow the wave to interact twice with the same scatterer. Wood's theory predicts the velocity of sound reasonably accurately for 0.5% bubble concentration. This is of course less and less accurate as the concentration of scatterers increases. Velocity predicted by Wood's theory for 0.5%, 1% and 2% microbubble concentration were 1.32 µm/ms 0.94 µm/ms and 0.68 µm/ms respectively. It can be observed that Wood's theory can reasonably approximate the velocity of the sound at low microbubble concentrations. At 0.1% bubble concentration, the fit between the iterative Fullwave simulation method and the ISA model was much more satisfying, but the ISA model still underestimated the attenuation value predicted by the simulation model by 15%, as shown in FIGS. 11A and 11B. At 0.1%, microbubble concentration the magnitude of velocity was 1.41 µm/ms, which was reasonably accurate approximation.

It should be noted that multiple scattering in a medium constituted by a group of randomly or periodically distributed bubbles has been extensively studied, for simple air bubbles embedded in a soft matrix, using Foldy's model or the ISA (Ben Salem, I. et al., 2013, Leroy, V et al., 2009 and 2008, Bretagne, A. et al., 2011). However, no such work had been conducted for ultrasound contrast agents, exhibiting a specific viscoelastic behavior due to their lipid shell. Additionally, the iterative Fullwave simulation method described and validated herein does not rely on intrinsic approximations on the concentration of micro-bubbles, contrary to the ISA. With a large number of simulation iterations, it is possible to accurately describe the exact behavior of wave transport in moderately concentrated populations of free ultrasound contrast agent microbubbles. The computational cost of performing such a large number of iterations can be taken into account. The total number of computations increases with the density of microbubbles since the pressure scattered by each bubble must be calculated for each iteration, in order to define the source terms for the next iteration. It can be observed from FIGS. 8A, 8B and 9 that the rate of convergence decreases with an increasing number of bubbles, which is to be expected. A higher density of microbubbles will lead to a higher number of iterations, thus delaying the time required to reach convergence. Nevertheless, the iterative Fullwave simulation method is the first simulation method that can model the complex phenomena related to multiple scattering physics of ultrasound by ultrasound contrast agents. Additionally, it should be understood that the iterative Fullwave simulation method described herein does not account for the microbubbles interacting with each other or with microbubbles adhering to targeted surfaces.

The results indicate that multiple scattering of ultrasound in a medium with randomly distributed microbubbles can be modeled using the iterative Fullwave simulation method, which combines propagation modeling and microbubble modeling. This method developed for 2-D simulations can be extended to 3-D simulations because the scattering at each individual bubble surface is evaluated separately, which automatically accounts for the expected additional multiple scattering in 3-D simulations. In addition, since this is a full-wave equation based method, the ultrasound field is described for all points in space and time for the domain.

The inter-elemental matrix of a system is a useful tool because the output of the system can be predicted for any input acoustic pulse. For a multiple scattering medium, important characteristics such as the scattering mean free path can be determined using the inter-elemental matrix. As described below, the accurate determination of the inter-elemental matrix in a bubbly medium can open up the possibility of evaluating the micro-architectural properties of vascular networks in which contrast agent microbubbles are injected.

There are significant differences between the microvasculature of cancerous and benign tissue, and the ability to distinguish them by quantifying the microvascular architectural properties non-invasively is attractive for medical diagnosis. Described herein is a method for the quantification of the microvascular architecture in terms of the mean distance between vessels, and the vasculature anisotropy ratio using multiple scattering of ultrasound from microbubbles injected in the vasculature. The results reported below are based on data collected from twenty-one tumor-bearing rats. The scattering mean free path (L) is computed from the diffusion constant (D) calculated from the time evolution of the incoherent intensity, which is obtained using the inter-elemental response matrix (IRM) (also referred to herein as an "inter-elemental matrix") acquired with a linear transducer array. Significant differences can be observed between values of L for tumor and healthy tissue. The measured values of L correspond to the estimated mean distance between vessels, indicating that this method can be used to quantify the vessel density. It is also demonstrated that a 1-D map of the scattering mean free path L can be produced by acquiring multiple sub-IRMs using a sub aperture translated along the array. It is also shown that the scattering mean free path can be used to quantify the anisotropy of a vascular network.

It was previously demonstrated that, at clinically relevant concentrations of ultrasound contrast agents, it is possible to measure the distance between two 200 μm diameters tubes, separated by distances as small as 50 μm [35], by taking advantage of the multiple scattering of ultrasound waves by the population of microbubbles. This measurement (e.g., using the iterative Fullwave simulation method described above) relies on considering the diffusive behavior of an acoustic wave in a population of microbubbles. By measuring the diffusion constant (D) and the scattering mean free path (L) of the wave in such a complex medium, it is possible to assess the distance between microvessels. Furthermore, it has been demonstrated on Fisher-344 rats in vivo, that the scattering mean free path L was significantly different in tumor and healthy tissue [36].

As described below, the scattering mean free path L can be correlated to the microvascular density, and the anisotropy of L can be used to characterize the anisotropy of the vasculature. High resolution micro-CT scans and a phantom experiment have been used to verify that the scattering mean free path corresponds to mean distance between the vessels. To quantify the anisotropy, the scattering mean free path along two perpendicular orientations (e.g., coronal and transverse) was measured. A ratio of scattering mean free path along these two orientations was computed, and this ratio is shown to be a metric of the anisotropy of the vasculature. This method was used by Du et al. [37] to quantify trabecular bone anisotropy.

Microbubble Agent Preparation

Contrast agent microbubbles were prepared by combining 1,2-distearoyl-sn-glycero-3-phosphocholine (DSPC) and 1,2-distearoyl-sn-glycero-3-phosphoethanolamine-N-[methoxy (polyethylene glycol)2000] (DSPE-PEG2000) (Avanti Polar Lipids; Alabaster, Ala., USA) in a 9:1 molar ratio. This solution was dissolved in a phosphate-buffered saline (PBS)-based excipient solution containing 15% (v/v) propylene glycol and 5% (v/v) glycerol for a final lipid concentration of 1.0 mg/mL. 1.5 ml of resultant solution was then added to 3 mL glass vials. The headspace air from the vial was then exchanged with decafluorobutane (DFB) gas (FluoroMed; Round Rock, Tex., USA). Microbubbles were formed after vigorous shaking of these vials for 45 seconds using a Vialmix mixer (Bristol-Myers-Squibb; New York, N.Y., USA). Detailed procedure to prepare these lipid-shelled microbubbles was described by Streeter et al [38].

The microbubbles solution was diluted in a ratio of 1:10 with saline for the multiple scattering acquisition (or 1:1 for acoustic angiography) and the diluted microbubble solutions was infused through the tail vein of the animals at a rate of 30 μL/min during the data acquisition. The microbubble concentration was estimated to be around $5 \times 10^7$ microbubbles/ml for the in-vivo experiments assuming blood volume in rat to be around 20 ml.

Animals

Twenty-one female Fischer-344 rats (Charles River Laboratories, Inc.; Wilmington, Mass., USA) were used. The animals were handled according to National Institute of Health guidelines. Fibrosarcoma tumors were grown in the right flank by subcutaneously implanting 1 $mm^3$ of tumor tissue fragment from donor animals. A 24-gauge catheter was inserted into the animal's tail vein for the administration of the contrast agent solution. The animal's right flank (tumor side) and the contralateral control side were shaved and ultrasound gel was placed between the transducer and the animal's skin to ensure good coupling during the data acquisition.

The animals were first anesthetized in an induction chamber by introducing a vaporized 5% isoflurane-oxygen mixture, before lowering the isoflurane concentration to 2.5-2% and placing the animal on a heated pad for data acquisition. The size of the tumor at the time of data acquisition was estimated using B-mode imaging (ellipsoid volume from sagittal and transverse planes of the largest tumor cross-section).

In-Vitro Phantom Experiment

Figure 12:
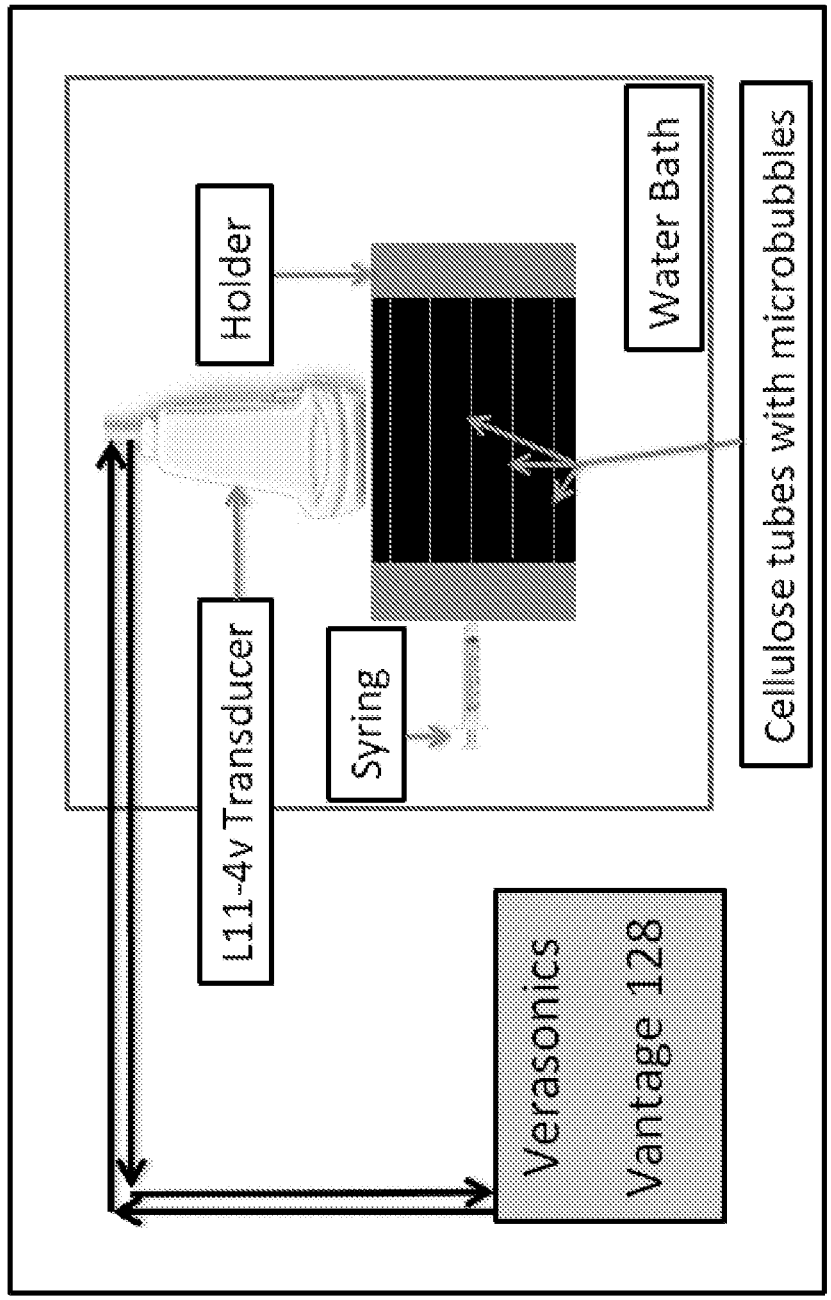
FIG. 12 illustrates a schematic diagram of the experimental setup for in-vitro phantom experiment according to an example described herein.

To validate how the scattering mean free path is representative of the mean distance between vessels at low microbubble concentrations, in-vitro experiments with a cellulose tube phantom were performed. A schematic diagram of the experimental setup is shown in FIG. 12. The phantom consisted of five equidistant cellulose tubes, placed in a water bath, separated by a distance precisely controlled using a specifically designed holder. The custom designed holder kept the tubes separated by a distance of 50 µm to 300 µm with a step size of 50 µm. Each cellulose tube (Spectrum Labs; Rancho Dominguez, Calif., USA) was 200 µm in diameter. The microbubble concentration was $5 \times 10^7$ microbubbles/ml.

Inter-Elemental-Response Matrix (IRM)

It should be understood that the inter-elemental-response matrix (or "inter-elemental matrix") described below is referred to above as a "response matrix," for example with regard to FIGS. 1 and 2. A Verasonics L11-4 linear array transducer, connected to a Verasonics 128 Vantage scanner (Verasonics, Inc., Kirkland, Wash., USA) operating at 7.8 MHz was used to acquire the IRM. The IRM is a 3-dimensional matrix containing the backscattered signals recorded over the entire array for signals transmitted consecutively by every single element of the array, one at a time.

All 128 elements of the array were sequentially used to transmit a 2-cycle Gaussian pulse with peak-to-peak pressure 300 kPa. For each transmit event, all 128 elements recorded backscattered echoes simultaneously for 50 microseconds. The IRM was recorded using the sampling frequency of 62.5 MHz. The acquired IRM has dimensions 128×128×3125, where 3125 is the number of time points. Acquisitions were obtained on both the tumor and control sides in two perpendicular orientations (coronal and transverse). It was ensured that these two planes approximately pass through the center of the tumor (largest cross-section) using B-mode imaging. The IRM was acquired for the tube phantom experiment following the same procedure, by placing the array in a plane parallel to plane of the tubes.

Acoustic Angiography

Acoustic angiography images were acquired with a modified 30 MHz Visual Sonics Vevo 770 single-element transducer with a confocal 4 MHz annular element added [39]. Contrast images were acquired by transmitting with the low frequency (4 MHz) element and receiving broadband superharmonic signals with the high frequency (30 MHz) element during an infusion of microbubbles, which were administered through the tail vein at a rate of $1.5 \times 10^8$ bubbles/minute. 3D images were acquired with a step size of 100 µm, averaging two frames in every location, at a frame rate of four frames per second.

Micro-CT Scan

After euthanasia via isoflurane overdose, the rats were perfused with warm saline mixed with 2% liquid dish soap through the left ventricle. BriteVu contrast (Scarlet Imaging, Murray, Utah, USA) was mixed with 100 mL of water and 2% liquid dish soap, and heated to 80° C. for 5-10 minutes before injection. After perfusion with the contrast material, specimens were allowed to harden overnight at 4° C. before micro-CT imaging with a SCANCO µCT 40 scanner (Scanco USA Inc., Wayne, Pa., USA). SCANCO µCT 40 is a high-resolution desktop cone-bean X-ray scanner designed for specimens with a top resolution of 6 µm.

To extract quantitative information from the micro-CT data, a 3D volume of the vasculature was reconstructed using volumetric reconstruction software, NRecon (Bruker micro CT, Kontich, Antwerp, Belgium). The volume was then binarized removing the background noise using CTAn software package (Bruker micro CT, Kontich, Antwerp, Belgium). The detailed procedure followed for image reconstruction was described by Lee et al. [40]. The mean distance between the vessels in 3D was computed from the binarized set. In order to calculate the mean distance between the vessels, a point on the vessel was picked and, then Euclidian distance between that point and the nearest point of the other vessel in the direction of propagation was computed. The mean distance between vessels for the whole tumor was then computed by averaging all the computed distances.

Monte-Carlo Simulations

In a highly diffusive medium such as a microbubble population, the propagation of waves scattered multiple times can be treated as a random walk process [41]. Using this assumption, the multiple scattering interactions of ultrasound wave with contrast agent microbubbles was simulated to estimate the scattering mean free path. High resolution CT-scan images for these simulations were used. Those 3-D images of the vasculature were binarized and then converted into maximum intensity 2-D projections.

In the simulation, the vessels from the 2D image were then randomly populated with uniformly distributed microbubbles at a concentration equivalent to $5 \times 10^7$ microbubbles/ml. During each iteration of the simulation, a particle was assumed to be traveling in the direction of propagation. Every time it collided with a microbubble, it was scattered. The probability for the particle to be scattered in a particular direction was determined by simulating scattering by a single microbubble using the iterative Full-wave simulation method described above [35]. This simulation approach combines a full-wave model which describes nonlinear propagation and scattering interactions in a heterogeneous attenuating medium [42] and a Paul-Sarkar model that describes the nonlinear interactions between an acoustic field and an isolated lipid-shelled microbubble [43]. In this simulation, the diameter of the scatterer (microbubble) was set to 1 micron and receivers were placed in a circle (2-D simulation) around the scatterer. The scatterer was insonated with a plane wave and the received signal on each transducer was normalized to estimate the probability of scattering in each direction.

During the iteration of the simulation, it was assumed that the particle continued to travel in the direction of propagation until it collided with microbubble. The iteration of the simulation was continued until the particle exited the medium, which can happen in any number of collisions, from zero to infinity. The total number of collisions was restricted to $10^4$ to avoid the simulations from going into an infinite loop, although this was unlikely to happen at low concentrations. Particles typically excited the medium after 287 collisions on average with a standard deviation of 32. The scattering mean free path (L) was defined as the mean distance travelled by the particles between collisions before exiting the medium. Mean L value was updated at the end of iteration. The simulation was continued until convergence. Tolerance of the simulation was set to 0.1 micron. The value of the scattering mean free path predicted using the multiple scattering was of order of 10's of microns. Thus a tolerance of 0.1 micron was less 1% of the expected value of the scattering mean free path. Convergence was obtained in $3.2 \times 10^5$ iterations on an average with a standard deviation of 56,821.

Monte-Carlo simulations to estimate scattering mean free path were also performed on maximum intensity projection of acoustic angiography (AA) 3D images. Because the resolution of AA images is lower compared to micro-CT scan images, higher values of the estimated scattering mean free path were expected.

Scattering Mean Free Path

A time shift was applied to all backscattered signals in the IRM along the time dimension such that the first backscattered echo arrival occurs at time t=0 for all emitter-receiver pairs. Each time signal of the IRM (H) can be represented by $h_{ij}(t)$, where i is the emitter number and j the receiver number. The signal is then divided into overlapping time windows (each 10 μs long with 50% overlapping). The backscattered intensity $I_{ij}(T)$ is calculated over each time window where T the is time at the center of the time window, and Δ is the width of the time window. The width of the time window was chosen based on the central frequency such that it spans over one scattering interaction, typically 1 to 2 wavelengths.

$$I_{ij}(T) = \int_{t_0(T)}^{t_0(T)+\Delta} h_{ij}^2(t)dt \quad (14)$$

The average backscattered intensity I (r, T) was calculated by averaging the backscattered intensity over transducer-receiver couples separated by the same distance (r=|i−j|×w). w is the pitch of the transducer array (w=0.3 mm). In order to separate the coherent and incoherent contributions to the intensity, the H matrix is transformed into an antisymmetric matrix M such that $m_{ij}=h_{ij}$ for i<j, $m_{ij}=-h_{ij}$ for i>j and $m_{ij}=0$ for i=j. The backscattered intensity $I_{ij}^A(T)$ and the averaged backscattered intensity $I^A(r, T)$ was then calculated from the antisymmetric matrix following a similar procedure. The coherent $I_{coherent}(r, T)$ and incoherent $I_{incoherent}(r, T)$ intensities were extracted by respectively adding or subtracting the intensities resulting from the matrices H and M [44].

$$I_{coherent}(r, T) = \frac{I(r, T) - I^A(r, T)}{2} \quad (15)$$

$$I_{incoherent}(r, T) = \frac{I(r, T) + I^A(r, T)}{2} \quad (16)$$

In the diffusive regime, the incoherent intensity can be expressed as a function of the diffusion constant D:

$$I_{incoherent}(r, T) = I(T) \times \exp\left(-\frac{r^2}{4DT}\right). \quad (17)$$

The Diffusion constant was then calculated by fitting a Gaussian curve to the incoherent intensity $I_{inc}(r, T)$. In the near-field, D is related to the transport mean free path $L^T$ by the following equation [45], [46]:

$$D = \frac{V_E \times L^T}{3}, \quad (18)$$

where, $V_E$ is transport velocity, i.e. the velocity at which the energy is diffused in the diffusive regime, and $L^T$ is the transport mean free path. The elastic mean free path (L*) is related to transport mean free path by the following equation:

$$L^T = \frac{L^*}{1 - \overline{\cos\theta}}. \quad (19)$$

The elastic mean free path is the characteristic length of the exponential decay of the coherent wave, i.e., the part of the wave that, on average, propagates in the initial direction. $\overline{\cos\theta}$ is the average of the cosine of the scattering angle calculated for a single scatterer using the methodology developed by Tourin et al. [46]. For an isotropic scatterer like a microbubbles [47] ($\overline{\cos\theta}\approx0$), $L^T\approx L^*\approx L$. Where L is the scattering mean free path, which is a measure of the mean distance between two scattering interactions.

1-D Mapping of Scattering Mean Free Path

In order to obtain more local measurements, multiple sub-IRMs along the length of the array were acquired instead of a single IRM. This could be achieved by using a subset of elements of the linear array and by moving the sub-aperture along the tumor, recording the IRM at each location. To make the process faster, the entire 128×128×N IRM was acquired, and was then split into sub-IRMs. For ease of matrix manipulation, the sub-aperture size can optionally be kept as an odd number. It was observed that the amplitude of the received signal significantly diminishes when the receiver is far away from the transmitting element. It was observed that it reduces by order of magnitude $10^3$ within 16 elements on either side of the transmitting element. Thus, a sub-aperture size of 33 was used. Each sub-IRM had dimensions of 33×33×N. For example, in order to obtain the first sub-IRM, the signals backscattered on the first 33 elements for pulses transmitted by first 33 elements were considered. The 2' sub-IRM consisted of the backscattered echoes collected by element number 2 to element number 34, for pulses transmitted by the same set of elements, the $3^{rd}$ sub IRM consisted of the backscattered echoes collected by element number 3 to element number 35, for pulses transmitted by the same set of elements, and so on. In the near field, the wave field can still be considered collimated, and the local value of diffusion constant could be measured from the 33×33×N sub-IRMs, thereby allowing the estimation of a fairly local scattering mean free path. This enabled the generation of 1-D maps of the scattering mean free path along the length of the array. The span of the mapped region is restricted to the length of the array. In order to map larger geometries, the array could be translated along the tumor. This disclosure contemplates that the choice of resolution for 1D mapping the Diffusion constant can be application dependent. The fewer the elements in each sub-IRM, the higher the resolution along the axis of the transducer will be. Choosing too few elements, however, can lead to incorrect estimation of diffusion constant. If too few elements are selected, the visualization of the diffusive halo is incorrect, and thus it leads to incorrect fitting of Gaussian curve resulting in incorrect measurement of diffusion constant.

Statistics

Statistical analyses were performed using Matlab 2016 a (MathWorks Inc., Natick, Mass., USA). D'Agostino-Pearson was used to verify the normality of data distributions. Unpaired t-tests were used to test hypotheses. Statistical significance was defined as a maximum of $p<0.05$.

For all 21 rats, the mean tumor volume was 360.54 mm$^3$ and the median tumor volume was 144.11 mm$^3$. The volume of the smallest tumor was 50.91 mm$^3$ and the volume of the largest tumor was 2349.7 mm$^3$. All 21 rats were imaged with the Verasonics system on the tumor and control sides along one orientation (transverse plane), and 17 of the rats were imaged in 2 perpendicular orientations (transverse and coronal). Acoustic angiography was performed on control side and tumor side for 16 rats. Full acoustic angiography data was not able to be acquired for 5 rats: 2 included data from only 1 side (tumor or control), and for 3 rats, acoustic angiography was not performed on either side due to experimental protocols due to time constraints (maximum anesthesia time of one hour). Micro-CT scans were performed on 2 tumors.

Diffusion Constant and Anisotropy Ratio (In-Vivo Experiments)

For the 16 tumor-bearing rats, the mean tumor diameter was 7.82±3.044 mm, and the mean tumor volume was 360.54±508 mm$^3$ (range 50.91 mm$^3$ to 2349.7 mm$^3$). FIG. 13A illustrates the D values obtained for both orientations for control and tumor flanks ($n_{control}$=18; $n_{tumor}$=16). Significant differences were observed for D values obtained in the transverse and coronal orientations for control regions (transverse: 1.61±0.51 mm$^2$/μs, coronal: 1.05±0.31 mm$^2$/μs, p<0.05). However, for tumors, there was no significant difference along the two orientations (transverse: 0.67±0.22 mm$^2$/μs, coronal: 0.61±0.28 mm$^2$/μs, p>0.05). The D values for control and tumor, combining both orientations, were found to be 1.38±0.51 mm$^2$/μs and 0.65±0.27 mm$^2$/μs, respectively. The anisotropy ratio of control and tumor regions are compared in FIG. 13B. The closer the anisotropy ratio is to one, the higher the isotropy of the tissue's vascular network. It is evident that control tissue exhibits significantly higher anisotropy ratios than tumor-bearing tissue, with ratios of 1.62±0.911 vs 1.13±0.51, respectively (p<0.05).

Vascular Density

Figure 14A:
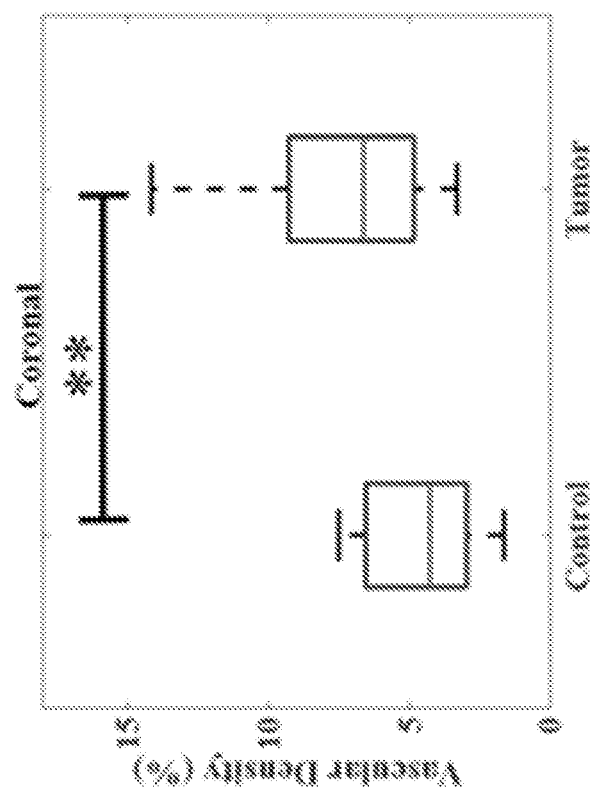
FIGS. 14A and 14B illustrate that vascular density (VD) was found significantly higher for tumors compared to controls, in both the coronal (shown in FIG. 14A) and transverse (shown in FIG. 14B) slices corresponding to the Inter-element response matrix (IRM) acquisitions.
Figure 14B:
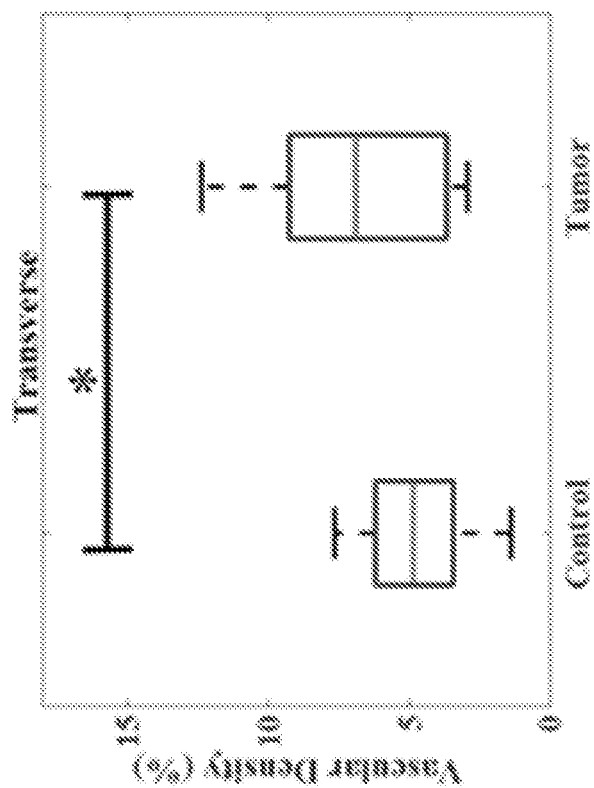

In both the coronal and transverse slices corresponding to the IRM acquisitions, the VD obtained from AA were significantly higher in tumors (n=14) compared to controls (n=13), as shown in FIGS. 14A and 14B. The vascular density for control in the transverse and coronal plane was observed to be 4.82±1.871% and 4.712±1.96%. Whereas, the vascular density for tumor in the transverse and coronal plane was observed to be 7.21±3.054% and 6.594±3.046%.

In-Vitro Experiments

Figure 15:
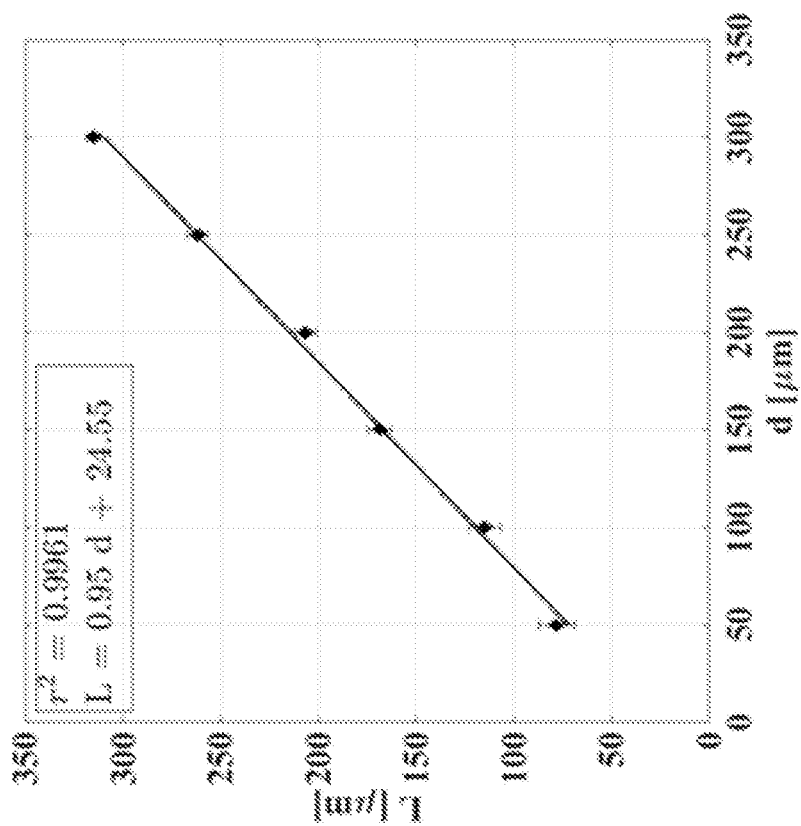
FIG. 15 illustrates the comparison between values of L (from in vitro experiment) and distance (d) between the tubes. Ten (10) readings were recorded for each value of d. Error bars indicates mean value ±standard deviation.

Experimentally determined values of the scattering mean free path shows excellent correlation with the actual distance between the tubes (Linear regression: $r^2$=0.9961, p=0.0076), as shown in FIG. 15. These results are consistent with previously reported results [36] which validates how scattering mean free path is a measure of the mean distance between the tubes when the concentration of microbubble is sufficiently low (5×10$^7$ microbubbles/ml). As observed in the FIG. 15, value of L slightly underestimates the actual distance between the tubes.

Scattering Mean Free Path Mapping

Figure 16A:
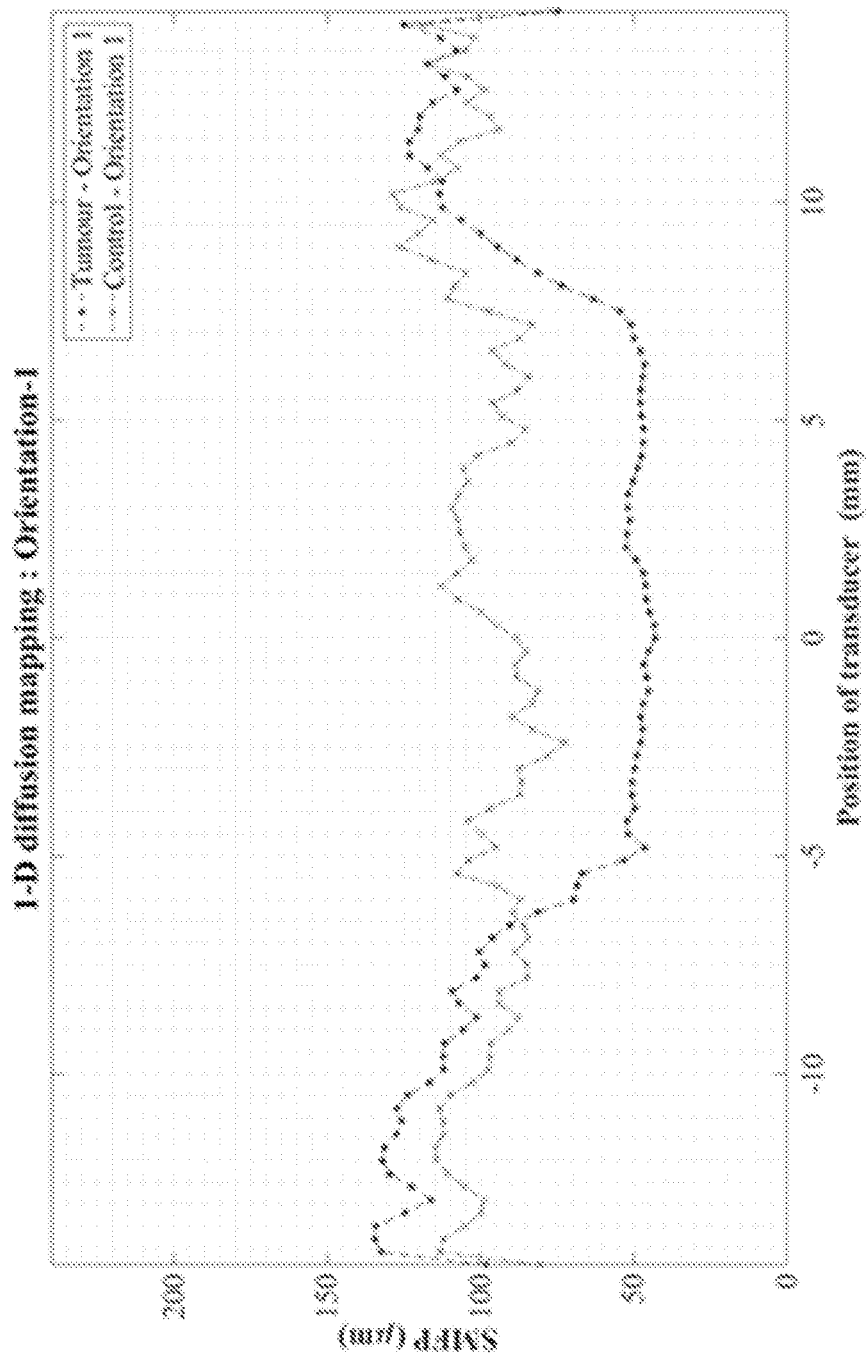
FIG. 16A and 16B illustrate scattering mean free path map along both of the orientations (Orientation-1=transverse plane shown by FIG. 16A; Orientation-2=coronal plane shown by FIG. 16B) for tumor and control.
Figure 16B:
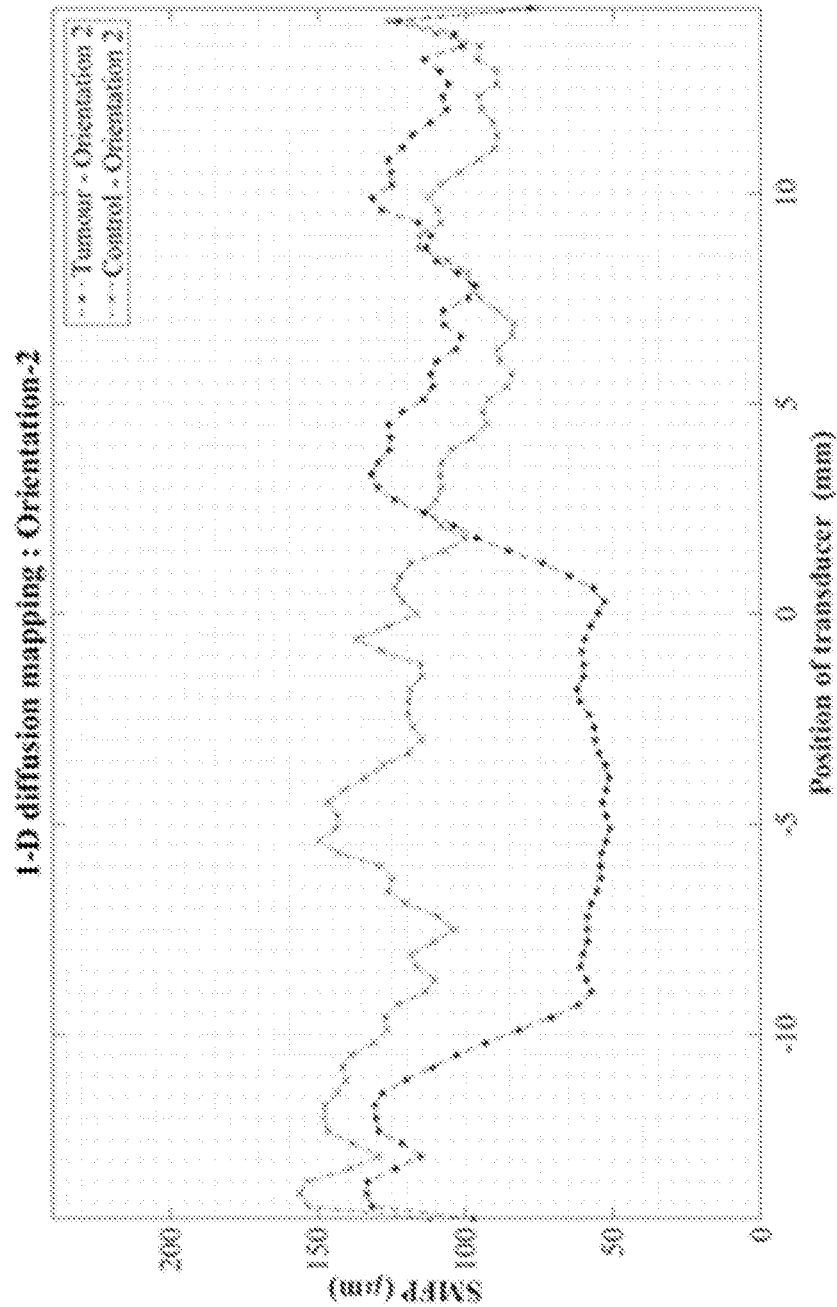
Figure 17B:
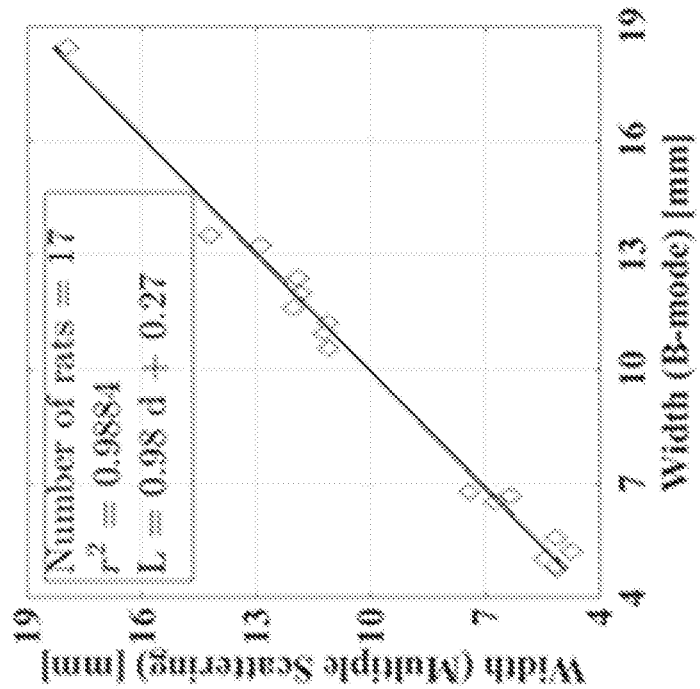
FIG. 17B illustrates the comparison between values of width measured from B-mode images and width measured using 1-D mapping.
Figure 17A:
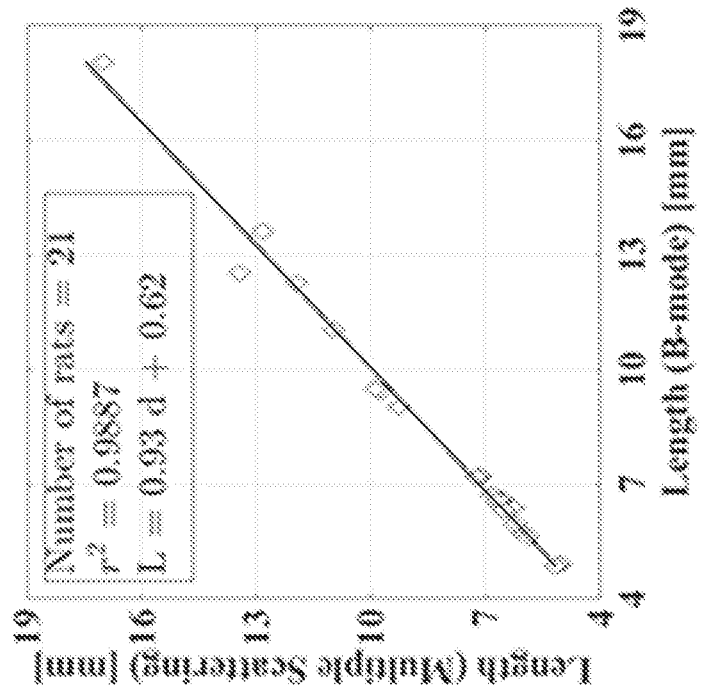
FIG. 17A illustrates the comparison between values of length measured from B-mode images and length measured using one-dimensional (1D or 1-D) mapping.

FIGS. 16A (Orientation-1=transverse plane) and 16B (Orientation-2=coronal plane) shows 1-D maps of the scattering mean free path for one of the tumors and corresponding contralateral (control) side along both orientations. A significant dip can be observed in the values of L on the tumor side. FIGS. 17A and 17B show a comparison between the length (along sagittal plane) and width (along transverse plane) of the tumor as measured with the scattering mean free path, with the length and width determined using B-mode imaging. A significant correlation can be observed between value of length and width determined using both techniques (Transverse Plane: $r^2$=0.98, Sagittal Plane: $r^2$=0.98).

Figure 18A:
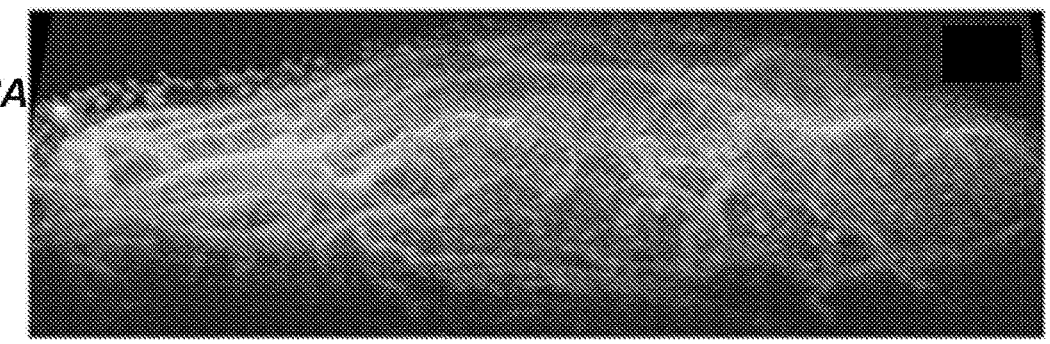
FIG. 18A is the maximum intensity projection of an Acoustic Angiography image of a tumor.
Figure 18B:
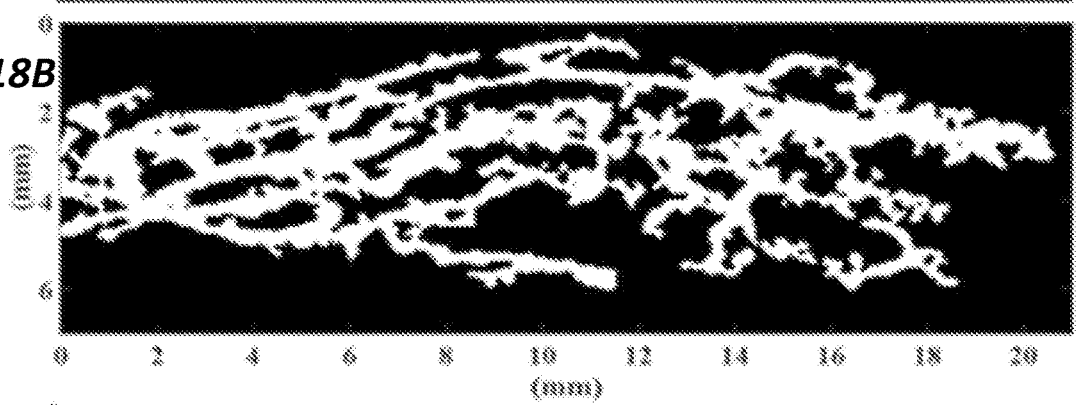
FIGS. 18B and 18C illustrate binarization (shown in FIG. 18B) and skeletonization (shown in FIG. 18C) of the Acoustic Angiography image shown in FIG. 18A.
Figure 18C:
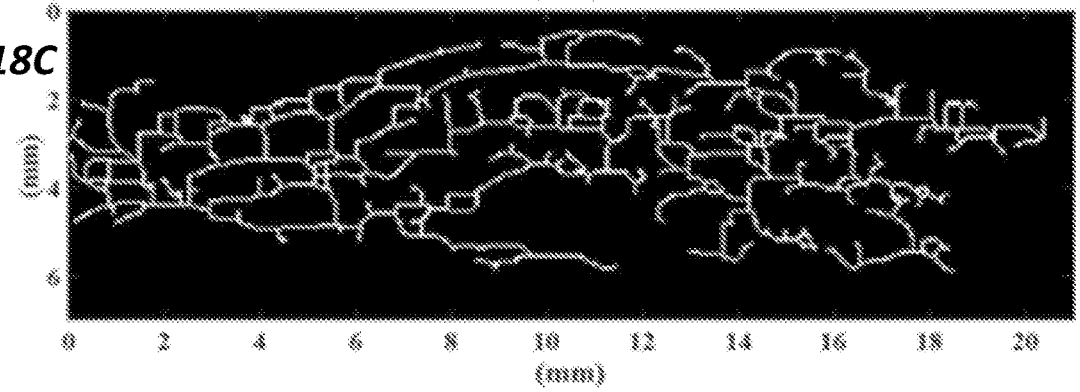
Figure 19:
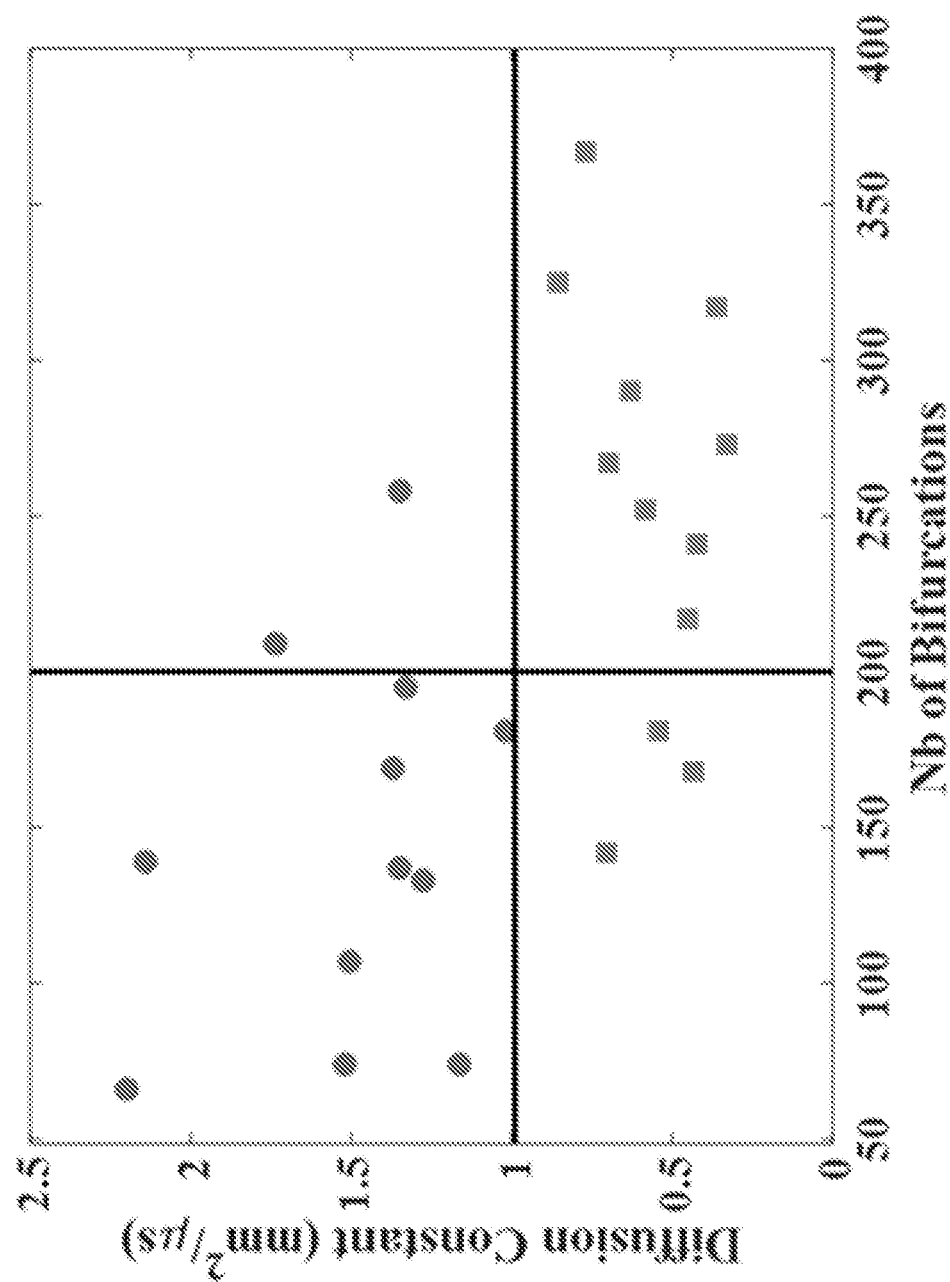
FIG. 19 illustrates the comparison between Diffusion Constant (measured using the IRM) and number of bifurcations measured from binarizing and skeletonizing the acoustic angiography as shown in FIGS. 18A-18C.

FIG. 18A shows maximum intensity projection of an Acoustic Angiography image of a tumor. FIG. 19 illustrates the comparison between Diffusion Constant (measured using the IRM) and number of bifurcations measured from binarizing (shown in FIG. 18B) and skeletonizing (shown in FIG. 18C) the acoustic angiography image (shown in FIG. 18A).

Figure 20:
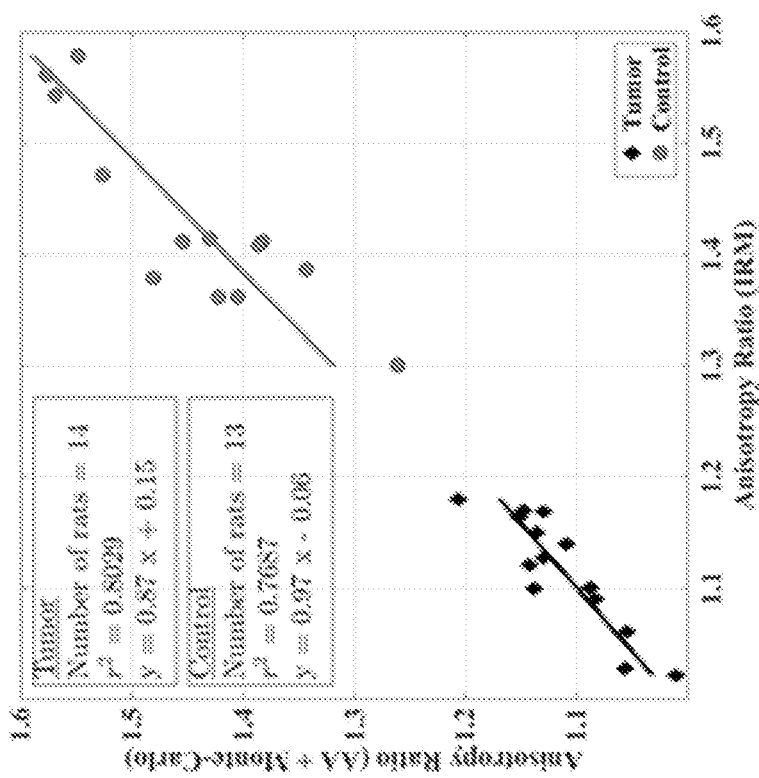
FIG. 20 illustrates the comparison between the anisotropy ratio computed from values of scattering mean free path measured from the IRM ("IRM") and the anisotropy ratio computed from values of scattering mean free path determined using Monte-Carlo simulations on AA images ("AA+ Monte Carlo").

FIG. 20 shows comparison between anisotropy ratio evaluated from values of scattering mean free path obtained from IRM and anisotropy ratio computed from values of scattering mean free path determined by performing Monte-Carlo analysis on acoustic angiography images. Moderately strong correlation is observed between two set of values although individual values of scattering mean free path computed using two techniques are significantly different.

Using the techniques described above, it is possible to successfully distinguish between tumor and control tissue in terms of the nominal values of the scattering mean free path, and the anisotropy of the scattering mean path measured using ultrasound multiple scattering by microbubbles. The results above validate how the scattering mean free paths is a measure of the mean distance between vessels at low bubble concentration.

The techniques described above allows a semi-local estimation of the scattering mean free path. Accordingly, it is not possible to obtain images using the techniques described above. The Diffusion Constant is function of the micro-architectural properties of the angiogenic microvasculature; however, the Diffusion Constant is not as local as other micro-architectural properties, as it relies of multiple scattering events occurring over multiple wavelengths. Although no images can be computed, the information extracted is quantitative, and it is possible to detect distances between tubes well below the wavelength (e.g., as small as 50 microns). Combining images obtained with acoustic angiogarphy (or other imaging modality), 1D Diffusion constant mapping, and estimation of the anisotropy of the scattering mean free path can provide a comprehensive set of data. Such comprehensive data can improve the specificity of ultrasound diagnosis. This disclosure contemplates that such comprehensive data can also be used to monitor the response to anti-angiogenic treatments.

The computational time need for the data processing to obtain the quantitative parameters described herein is of the order of a few minutes (on a desktop with a dual 2.7 GHz Intel premium core i7 processor and 16GB RAM it took average 8 minutes). This includes the acquisition time. It is expected that advanced computing technologies, like parallel processing can decrease this time to few seconds.

References

[1] J. Folkman, D. M. J. Long, and F. F. Becker, "Growth and metastasis of tumor in organ culture.," *Cancer*, vol. 16, pp. 453-467, April 1963.

[2] R. K. Jain, J. D. Martin, and T. Stylianopoulos, "The role of mechanical forces in tumor growth and therapy.," *Annu. Rev. Biomed. Eng.*, vol. 16, pp. 321-346, Jul. 2014.

[3] R. K. Jain, "Antiangiogenesis strategies revisited: from starving tumors to alleviating hypoxia.," *Cancer Cell*, vol. 26, no. 5, pp. 605-622, November 2014.

[4] P. Carmeliet and R. K. Jain, "Angiogenesis in cancer and other diseases.," *Nature*, vol. 407, no. 6801, pp. 249-257, September 2000.

[5] B. Nico, V. Benagiano, D. Mangieri, N. Maruotti, A. Vacca, and D. Ribatti, "Evaluation of microvascular density in tumors: pro and contra.," *Histol. Histopathol.*, vol. 23, no. 5, pp. 601-607, May 2008.

[6] A. Eberhard, S. Kahlert, V. Goede, B. Hemmerlein, K. H. Plate, and H. G. Augustin, "Heterogeneity of angiogenesis and blood vessel maturation in human tumors: implications for antiangiogenic tumor therapies.," *Cancer Res.*, vol. 60, no. 5, pp. 1388-1393, March 2000.

[7] P. Carmeliet, "Angiogenesis in life, disease and medicine.," *Nature*, vol. 438, no. 7070, pp. 932-936, December 2005.

[8] N. Weidner, J. Folkman, F. Pozza, P. Bevilacqua, E. N. Allred, D. H. Moore, S. Meli, and G. Gasparini, "Tumor angiogenesis: a new significant and independent prognostic indicator in early-stage breast carcinoma.," *J. Natl. Cancer Inst.*, vol. 84, no. 24, pp. 1875-1887, December 1992.

[9] A. M. Al Murri, M. Hilmy, J. Bell, C. Wilson, A.-M. McNicol, A. Lannigan, J. C. Doughty, and D. C. McMillan, "The relationship between the systemic inflammatory response, tumour proliferative activity, T-lymphocytic and macrophage infiltration, microvessel density and survival in patients with primary operable breast cancer.," *Br. J. Cancer*, vol. 99, no. 7, pp. 1013-1019, October 2008.

[10] G. Gasparini, N. Weidner, P. Bevilacqua, S. Maluta, P. Dalla Palma, O. Caffo, M. Barbareschi, P. Boracchi, E. Marubini, and F. Pozza, "Tumor microvessel density, p53 expression, tumor size, and peritumoral lymphatic vessel invasion are relevant prognostic markers in node-negative breast carcinoma.," *J. Clin. Oncol.*, vol. 12, no. 3, pp. 454-466, March 1994.

[11] J. Concato, D. Jain, W. W. Li, H. A. Risch, E. M. Uchio, and C. K. Wells, "Molecular markers and mortality in prostate cancer.," *BJU Int., vol.* 100, no. 6, pp. 1259-1263, December 2007.

[12] C. Y. Li, S. Shan, Q. Huang, R. D. Braun, J. Lanzen, K. Hu, P. Lin, and M. W. Dewhirst, "Initial stages of tumor cell-induced angiogenesis: evaluation via skin window chambers in rodent models.," *J. Natl. Cancer Inst.*, vol. 92, no. 2, pp. 143-147, January 2000.

[13] N. Weidner, J. P. Semple, W. R. Welch, and J. Folkman, "Tumor Angiogenesis and Metastasis—Correlation in Invasive Breast Carcinoma," *N. Engl. J. Med.*, vol. 324, no. 1, pp. 1-8, January 1991.

[14] S. van der Bij, E. Schaake, H. Koffijberg, J. A. Burgers, B. A. J. M. de Mol, and K. G. M. Moons, "Markers for the non-invasive diagnosis of mesothelioma: a systematic review," *Br J Cancer*, vol. 104, no. 8, pp. 1325-1333, April 2011.

[15] J. Ehling, B. Theek, F. Gremse, S. Baetke, D. Mockel, J. Maynard, S.-A. Ricketts, H. Grüll, M. Neeman, R. Knuechel, W. Lederle, F. Kiessling, and T. Lammers, "Micro-CT Imaging of Tumor Angiogenesis: Quantitative Measures Describing Micromorphology and Vascularization," *Am. J. Pathol.*, vol. 184, no. 2, pp. 431-441, February 2014.

[16] T. J. A. Snoeks, C. W. G. M. Löwik, and E. L. Kaijzel, "'In vivo' optical approaches to angiogenesis imaging," *Angiogenesis*, vol. 13, no. 2. Dordrecht, pp. 135-147, June 2010.

[17] C. T. Leondes, Biomechanical systems technology (Volume 1) computational methods. River Edge, US: WSPC, 2007.

[18] J. G. Fujimoto, C. Pitris, S. A. Boppart, and M. E. Brezinski, "Optical Coherence Tomography: An Emerging Technology for Biomedical Imaging and Optical Biopsy," *Neoplasia*, vol. 2, no. 1-2, pp. 9-25, January 2000.

[19] B. J. Vakoc, D. Fukumura, R. K. Jain, and B. E. Bouma, "Cancer imaging by optical coherence tomography: preclinical progress and clinical potential," *Nat. Rev. Cancer*, vol. 12, no. 5, pp. 363-368, April 2012.

[20] S. H. Yun, G. J. Tearney, J. F. de Boer, N. Iftimia, and B. E. Bouma, "High-speed optical frequency-domain imaging," *Opt. Express*, vol. 11, no. 22, pp. 2953-2963, November 2003.

[21] F. Boschi, P. Marzola, M. Sandri, E. Nicolato, M. Galiè, S. Fiorini, F. Merigo, V. Lorusso, L. Chaabane, and A. Sbarbati, "Tumor microvasculature observed using different contrast agents: a comparison between Gd-DTPA-Albumin and B-22956/1 in an experimental model of mammary carcinoma," *Magn. Reson. Mater. Physics, Biol. Med.*, vol. 21, no. 3, pp. 169-176, 2008.

[22] W. A. Berg, "Combined Screening With Ultrasound and Mammography vs Mammography Alone in Women at Elevated Risk of Breast Cancer,"*Jama*, vol. 299, no. 18, p. 2151, May 2008.

[23] D. Maresca, I. Skachkov, G. Renaud, K. Jansen, G. van Soest, N. de Jong, and A. F. W. van der Steen, "Imaging Microvasculature with Contrast-Enhanced Ultraharmonic Ultrasound," *Ultrasound Med. Biol.*, vol. 40, no. 6, pp. 1318-1328, January 2017.

[24] S. R. Sirsi, M. L. Flexman, F. Vlachos, J. Huang, S. L. Hernandez, H. K. Kim, T. B. Johung, J. W. Gander, A. R. Reichstein, B. S. Lampl, A. Wang, A. H. Hielscher, J. J. Kandel, D. J. Yamashiro, and M. A. Borden, "Contrast Ultrasound Imaging for Identification of Early Responder Tumor Models to Anti-Angiogenic Therapy," *Ultrasound Med. Biol.*, vol. 38, no. 6, pp. 1019-1029, June 2012.

[25] R. Gramiak and P. M. Shah, "Echocardiography of the Aortic Root.," *Invest. Radiol.*, vol. 3, no. 5, 1968.

[26] S. V. Setola, O. Catalano, F. Sandomenico, and A. Siani, "Contrast-enhanced sonography of the kidney," *Abdom. Imaging*, vol. 32, no. 1, pp. 21-28, October 2007.

[27] M. Fillon, "Contrast-Enhanced Ultrasound May Aid Prostate Cancer Detection," *JNCI J. Natl. Cancer Inst.*, vol. 105, no. 7, pp. 444-446, April 2013.

[28] R. P. Kedar, D. Cosgrove, V. R. McCready, J. C. Bamber, and E. R. Carter, "Microbubble contrast agent for color Doppler US: Effect on breast masses," *Radiology*, vol. 198, no. 3, pp. 679-686, March 1996.

[29] C. Balleyguier, P. Opolon, M. C. Mathieu, A. Athanasiou, J. R. Garbay, S. Delaloge, and C. Dromain, "New potential and applications of contrast-enhanced ultrasound of the breast: Own investigations and review of the literature," *Eur. J. Radiol.*, vol. 69, no. 1, pp. 14-23, January 2009.

[30] A. R. Sever, P. Mills, S. E. Jones, K. Cox, J. Weeks, D. Fish, and P. A. Jones, "Preoperative sentinel node identification with ultrasound using microbubbles in patients with breast cancer," *Am. J. Roentgenol.*, vol. 196, no. 2, pp. 251-256, February 2011.

[31] M. D'Onofrio, E. Barbi, C. F. Dietrich, M. Kitano, K. Numata, A. Sofuni, F. Principe, A. Gallotti, G. A. Zamboni, and R. P. Mucelli, "Pancreatic multicenter ultrasound study (PAMUS)," *Eur. J. Radiol.*, vol. 81, no. 4, pp. 630-638, April 2012.

[32] R. C. Gessner, C. B. Frederick, F. S. Foster, and P. A. Dayton, "Acoustic angiography: a new imaging modality for assessing microvasculature architecture.," *Int. J. Biomed. Imaging*, vol. 2013, p. 936593, 2013.

[33] S. E. Shelton, B. D. Lindsey, J. K. Tsuruta, F. S. Foster, and P. A. Dayton, "Molecular Acoustic Angiography: A New Technique for High-resolution Superharmonic Ultrasound Molecular Imaging.," *Ultrasound Med. Biol.*, vol. 42, no. 3, pp. 769-781, March 2016.

[34] S. E. Shelton, Y. Z. Lee, M. Lee, E. Cherin, F. S. Foster, S. R. Aylward, and P. A. Dayton, "Quantification of Microvascular Tortuosity during Tumor Evolution Using Acoustic Angiography.," *Ultrasound Med. Biol.*, vol. 41, no. 7, pp. 1896-1904, July 2015.

[35] A. Joshi, B. Lindsey, P. Dayton, G. Pinton, and M. Muller, "An iterative fullwave simulation approach to multiple scattering in media with randomly distributed microbubbles," *Phys. Med. Biol.*, March 2017.

[36] A. Joshi, S. Sarah, V. Papadopoulou, B. Lindsey, P. Dayton, and M. Muller, "In-vivo quantitative analysis of the angiogenic microvasculature in tumor-bearing rats using multiple scattering: A preliminary study," *J. Acoust. Soc. Am.*, vol. 140, no. 4, p. 3187, October 2016.

[37] H. Du, K. Mohanty, and M. Muller, "Microstructural characterization of trabecular bone using ultrasonic backscattering and diffusion parameters," *J. Acoust. Soc. Am.*, vol. 141, no. 5, p. EL445-EL451, May 2017.

[38] J. E. Streeter, R. Gessner, I. Miles, and P. A. Dayton, "Improving sensitivity in ultrasound molecular imaging by tailoring contrast agent size distribution: in vivo studies.," *Mol. Imaging*, vol. 9, no. 2, pp. 87-95, April 2010.

[39] R. Gessner, M. Lukacs, M. Lee, E. Cherin, F. S. Foster, and P. A. Dayton, "High-resolution, high-contrast ultrasound imaging using a prototype dual-frequency transducer: in vitro and in vivo studies.," *IEEE Trans. Ultrason. Ferroelectr. Freq. Control*, vol. 57, no. 8, pp. 1772-1781, August 2010.

[40] S. Lee, M. F. Barbe, R. Scalia, and L. E. Goldfinger, "Three-dimensional reconstruction of neovasculature in solid tumors and basement membrane matrix using ex vivo X-ray micro-computed tomography," *Microcirculation*, vol. 21, no. 2, pp. 159-170, February 2014.

[41] J. Page, I. Jones, H. Schriemer, M. Cowan, P. Sheng, and D. Weitz, "Diffusive transport of acoustic waves in strongly scattering media," *Phys. B Condens. Matter*, vol. 263, pp. 37-39, 1999.

[42] G. F. Pinton, J. Dahl, S. Rosenzweig, and G. E. Trahey, "A heterogeneous nonlinear attenuating full-wave model of ultrasound," *IEEE Trans. Ultrason. Ferroelectr. Freq. Control*, vol. 56, no. 3, pp. 474-488, March 2009.

[43] S. Paul, A. Katiyar, K. Sarkar, D. Chatterjee, W. T. Shi, and F. Forsberg, "Material characterization of the encapsulation of an ultrasound contrast microbubble and its subharmonic response: strain-softening interfacial elasticity model.," *J. Acoust. Soc. Am.*, vol. 127, no. 6, pp. 3846-3857, June 2010.

[44] A. Aubry and A. Derode, "Ultrasonic imaging of highly scattering media from local measurements of the diffusion constant: Separation of coherent and incoherent intensities," *Phys. Rev. E*, vol. 75, no. 2, p. 26602, February 2007.

[45] K. Busch, C. M. Soukoulis, and E. N. Economou, "Transport and scattering mean free paths of classical waves," *Phys. Rev. B*, vol. 50, no. 1, pp. 93-98, July 1994.

[46] Tourin, Derode, Peyre, and Fink, "Transport parameters for an ultrasonic pulsed wave propagating in a multiple scattering medium," *J. Acoust. Soc. Am.*, vol. 108, no. 2, pp. 503-512, August 2000.

[47] S. Hilgenfeldt, D. Lohse, and M. Zomack, "Response of bubbles to diagnostic ultrasound: a unifying theoretical approach," *Eur. Phys. J. B*, vol. 4, no. 2, pp. 247-255, July 1998.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A system, comprising:
an ultrasound transducer array configured to transmit a plurality of acoustic pulses into a medium, wherein the medium includes a vascular network populated by an ultrasound contrast agent comprising microbubbles, wherein each respective acoustic pulse is transmitted from one or more transducer elements of the ultrasound transducer array; and
a computing device comprising a processor and a memory operably coupled to the processor, wherein the memory has computer-executable instructions stored thereon that, when executed by the processor, cause the processor to:
receive a plurality of backscattered signals, wherein each backscattered signal is separately received by each of the plurality of transducer elements in the ultrasound transducer array in response to each respective acoustic pulse;
obtain a response matrix comprising the backscattered signals;
extract a coherent contribution to the backscattered signals from the response matrix and quantify a vessel density or an anisotropy metric of the vascular network based on the coherent contribution to the backscattered signals, or extract an incoherent contribution to the backscattered signals from the response matrix and quantify the vessel density or the anisotropy metric of the vascular network based on the incoherent contribution to the backscattered signals, wherein the backscattered signals are induced by the ultrasound contrast agent and the medium;
differentiate, based at least in part on the quantified vessel density or the quantified anisotropy metric, between healthy and tumoral tissues; and
provide the quantified vessel density or the quantified anisotropy metric on a display device.

2. The system of claim 1, further comprising an injection device configured to inject the ultrasound contrast agent into the medium.

3. The system of claim 2, wherein a concentration of the microbubbles is less than 0.5% ($5 \times 10^6$ microbubbles/mL) bubble concentration by volume.

4. The system of claim 2, wherein a concentration of the microbubbles is between 0.5% ($5 \times 10^6$ microbubbles/mL) and 2% ($2 \times 10^7$ microbubbles/mL) bubble concentration by volume.

5. The system of claim 1, wherein the backscattered signals are received at a subset of transducer elements of the ultrasound transducer array in response to each respective acoustic pulse.

6. The system of claim 1, wherein extracting the coherent contribution to the backscattered signals or extracting the incoherent contribution to the backscattered signals comprises determining a diffusion constant of the medium.

7. The system of claim 6, wherein the incoherent contribution to the backscattered signals is extracted from the response matrix, and wherein the diffusion constant of the medium is determined using the incoherent contribution to the backscattered signals.

8. The system of claim 6, wherein the coherent contribution to the backscattered signals is extracted from the response matrix, and wherein the diffusion constant of the medium is determined using the coherent contribution to the backscattered signals.

9. The system of claim 6, wherein the memory has further computer-executable instructions stored thereon that, when executed by the processor, cause the processor to estimate a scattering or transport mean free path using the diffusion constant of the medium.

10. The system of claim 9, wherein the memory has further computer-executable instructions stored thereon that, when executed by the processor, cause the processor to generate a map of the scattering or transport mean free path over a dimension of a tumor.

11. The system of claim 1, wherein the quantified vessel density is correlated to a scattering or transport mean free path, or the quantified vessel density is the number of blood vessels per unit of tissue volume.

12. The system of claim 1, wherein the quantified anisotropy metric is related to respective scattering or transport mean free paths for at least two orientations of the ultrasound transducer array.

13. The system of claim 12, wherein the ultrasound transducer array is rotated over the vascular network to obtain measurements in the at least two orientations.

14. The system of claim 1, wherein the system is a catheter or an ultrasound scanner.

15. The system of claim 1, wherein the acoustic pulses have a frequency of between 1 MHz and 15 MHz.

16. The system of claim 1, wherein the memory has further computer-executable instructions stored thereon that, when executed by the processor, cause the processor to detect or diagnose a tumor based on the quantified vessel density or the quantified anisotropy metric.

17. The system of claim 1, wherein the memory has further computer-executable instructions stored thereon that, when executed by the processor, cause the processor to detect the presence of angiogenesis based on the quantified vessel density or the quantified anisotropy metric.

18. The system of claim 1, wherein the vascular network comprises a plurality of blood vessels, and wherein a majority of the blood vessels of the vascular network have a diameter less than 1 millimeter (mm).

19. The system of claim 1, wherein the ultrasound transducer array comprises at least one of a two-dimensional, curved, or circular transducer.

20. The system of claim 1, wherein no images are created using the plurality of backscattered signals.

* * * * *